(12) United States Patent
Fujita et al.

(10) Patent No.: US 10,684,198 B2
(45) Date of Patent: *Jun. 16, 2020

(54) GUEST-COMPOUND-ENVELOPING POLYMER-METAL-COMPLEX CRYSTAL, METHOD FOR PRODUCING SAME, METHOD FOR PREPARING CRYSTAL STRUCTURE ANALYSIS SAMPLE, AND METHOD FOR DETERMINING MOLECULAR STRUCTURE OF ORGANIC COMPOUND

(71) Applicant: JAPAN SCIENCE AND TECHNOLOGY AGENCY, Kawaguchi-shi, Saitama (JP)

(72) Inventors: Makoto Fujita, Tokyo (JP); Yasuhide Inokuma, Tokyo (JP); Shota Yoshioka, Tokyo (JP); Junko Ariyoshi, Tokyo (JP)

(73) Assignee: JAPAN SCIENCE AND TECHNOLOGY AGENCY, Kawaguchi-shi, Saitama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/217,086

(22) Filed: Dec. 12, 2018

(65) Prior Publication Data

US 2019/0137367 A1    May 9, 2019

Related U.S. Application Data

(62) Division of application No. 14/426,809, filed as application No. PCT/JP2013/056370 on Mar. 7, 2013, now Pat. No. 10,190,952.

(30) Foreign Application Priority Data

Sep. 7, 2012 (JP) ................................. 2012-197911
Dec. 11, 2012 (JP) ................................. 2012-270199

(51) Int. Cl.
*C30B 29/54* (2006.01)
*G01N 1/28* (2006.01)
(Continued)

(52) U.S. Cl.
CPC ................. *G01N 1/28* (2013.01); *B05D 1/18* (2013.01); *C07D 307/92* (2013.01);
(Continued)

(58) Field of Classification Search
CPC ............................... C30B 29/54; C30B 29/65
See application file for complete search history.

(56) References Cited

U.S. PATENT DOCUMENTS 10,190,952 B2 * 1/2019 Fujita ..................... C30B 29/58
2003/0138940 A1 7/2003 Lemmo et al.

FOREIGN PATENT DOCUMENTS

CN      101319348 A    12/2008
JP      2000-086683 A   3/2000
(Continued)

OTHER PUBLICATIONS

M. Kawano et al., "Direct observation of crystalline-state guest exchange in coordination networks", Coordination Chemistry Reviews, 2007, vol. 251, pp. 2592-2605, cited in International Search Report of International Application No. PCT/JP2013/056370 dated May 7, 2013.

(Continued)

*Primary Examiner* — Robert M Kunemund
(74) *Attorney, Agent, or Firm* — Westerman, Hattori, Daniels & Adrian, LLP

(57) ABSTRACT

The present invention is a method for preparing a crystal structure analysis sample in which a molecule of an organic compound for which a molecular structure is to be determined, is arranged in pores and voids of a polymer-metal complex crystal in an ordered manner. The method includes (Continued)

immersing a polymer-metal complex crystal including a guest compound in a solvent solution that includes the organic compound, the polymer-metal complex crystal including a guest compound being the polymer-metal complex crystal comprising a polymer-metal complex that comprises a ligand having two or more coordinating moieties. A ratio of an amount of the guest compound (A) present in the pores and the voids to a total amount of the guest compound included in the pores and the voids being 60 mol % or more.

20 Claims, 16 Drawing Sheets

(51) Int. Cl.
  *C07D 401/14* (2006.01)
  *C07D 311/30* (2006.01)
  *C07D 307/92* (2006.01)
  *C30B 7/06* (2006.01)
  *C30B 29/58* (2006.01)
  *B05D 1/18* (2006.01)
  *G01N 23/207* (2018.01)
  *G01N 31/22* (2006.01)

(52) U.S. Cl.
  CPC .......... *C07D 311/30* (2013.01); *C07D 401/14* (2013.01); *C30B 7/06* (2013.01); *C30B 29/54* (2013.01); *C30B 29/58* (2013.01); *G01N 23/207* (2013.01); *G01N 31/22* (2013.01); *Y10T 428/249921* (2015.04)

(56) References Cited

FOREIGN PATENT DOCUMENTS

| | | |
|---|---|---|
| JP | 2006-188560 A | 7/2006 |
| JP | 2006-232738 A | 9/2006 |
| JP | 2008-214318 A | 9/2008 |
| JP | 2008-247884 A | 10/2008 |
| JP | 2010-090141 A | 4/2010 |
| WO | 2009/130987 A1 | 10/2009 |
| WO | 2011/062260 A1 | 5/2011 |

OTHER PUBLICATIONS

Extended (Supplemental) European Search Report (EESR) dated May 20, 2016, issued in counterpart European Patent Application No. 13835833.8.
Ohmori et al., "Crystal-to-Crystal Guest Exchange of Large Organic Molesules Within a 3D Coordination Network", J. A.C.S., 2004, pp. 126, 16292-16293.
Non-Final Office Action dated Jun. 28, 2017, issued in U.S. Appl. No. 14/426,809.
Final Office Action dated Jan. 2, 2018, issued in U.S. Appl. No. 14/426,809.
Non-Final Office Action dated May 17, 2018, issued in U.S. Appl. No. 14/426,809.
Notice of Allowance dated Sep. 13, 2018, issued in U.S. Appl. No. 14/426,809.

\* cited by examiner

GUEST-COMPOUND-ENVELOPING POLYMER-METAL-COMPLEX CRYSTAL, METHOD FOR PRODUCING SAME, METHOD FOR PREPARING CRYSTAL STRUCTURE ANALYSIS SAMPLE, AND METHOD FOR DETERMINING MOLECULAR STRUCTURE OF ORGANIC COMPOUND

CROSS-REFERENCE TO RELATED APPLICATIONS

This application is a divisional of U.S. application Ser. No. 14/426,809, filed on Mar. 9, 2015 now U.S. Pat. No. 10,190,952, which is a 371 of International Application No. PCT/JP2013/056370, filed on Mar. 7, 2013, which claims the benefit of priorities from the prior Japanese Patent Application No. 2012-270199, filed on Dec. 11, 2012, and Japanese Patent Application No. 2012-197911, filed on Sep. 7, 2012 the entire contents of which are incorporated herein by reference.

TECHNICAL FIELD

The present invention relates to a polymer-metal complex crystal including a guest compound that is useful as a material for preparing a crystal structure analysis sample that is used to determine the molecular structure of a trace amount of organic compound, a method for producing the same, a method for preparing a crystal structure analysis sample that utilizes the polymer-metal complex crystal including a guest compound, and a method for determining the molecular structure of an organic compound that utilizes a crystal structure analysis sample obtained using the method for preparing a crystal structure analysis sample.

BACKGROUND ART

In recent years, a physiologically active substance that is derived from a marine organism or the like and found in a trace amount has been expected to be a resource for agricultural chemicals, medicines, and the like (Patent Documents 1 and 2). Therefore, it has become very important to accurately and efficiently determine the molecular structure of such a trace amount of organic compound in order to develop a novel agricultural chemical or medicine, for example.

When producing an agricultural chemical or a medicine, it is necessary to accurately identify a trace amount of impurities included in the agricultural chemical, medicine, or raw material in order to improve safety.

It has also been desired to identify a trace amount of impurities included in a raw material used to produce electronic parts, and reduce the amount of impurities along with a recent improvement in performance of electronic parts.

Specifically, it has been desired to accurately and efficiently determine the molecular structure of a trace amount of organic compound in various fields.

X-ray single crystal structure analysis has been known as a method for determining the molecular structure of an organic compound. The molecular structure of an organic compound can be accurately determined using X-ray single crystal structure analysis when it is possible to prepare a high-quality single crystal.

However, when the amount of organic compound is very small, and it is impossible to obtain a sufficient amount of single crystal, it is difficult to employ X-ray single crystal structure analysis for determining the molecular structure of the organic compound. It is difficult to prepare a single crystal when the organic compound for which the molecular structure is to be determined is liquid at about room temperature (i.e., when the melting point of the organic compound is equal to or lower than room temperature).

RELATED-ART DOCUMENT

Patent Document

Patent Document 1: JP-A-2006-232738
Patent Document 2: JP-A-2010-090141

SUMMARY OF THE INVENTION

Technical Problem

The invention was conceived in view of the above situation. An object of the invention is to provide a polymer-metal complex crystal including a guest compound that makes it possible to prepare a crystal structure analysis sample that is useful for determining the molecular structure of a trace amount of organic compound, a method for producing the same, a method for preparing a crystal structure analysis sample, and a method for determining the molecular structure of an organic compound that utilizes a crystal structure analysis sample obtained using the method for preparing a crystal structure analysis sample.

Solution to Problem

The inventors of the invention conducted extensive studies in order to solve the above technical problem. As a result, the inventors found that a sample that is suitable for crystal structure analysis that is used to determine the molecular structure of a trace amount of organic compound can be efficiently prepared by utilizing a polymer-metal complex crystal including a guest compound that includes a polymer-metal complex having a three-dimensional network structure, and having pores and voids that are three-dimensionally arranged in the three-dimensional network structure in an ordered manner, wherein a specific guest compound is included in the pores and the like in an amount equal to or more than a given amount. This finding has led to the completion of the invention.

Several aspects of the invention provide the following polymer-metal complex crystal including a guest compound (see [1] to [8]), method for producing a polymer-metal complex crystal including a guest compound (see [10]), method for preparing a crystal structure analysis sample (see [11] to [20]), and a method for determining the molecular structure of an organic compound (see [21]).

[1] A polymer-metal complex crystal including a guest compound, the polymer-metal complex crystal including a polymer-metal complex that includes a ligand having two or more coordinating moieties, and a metal ion that serves as a center metal, the polymer-metal complex having a three-dimensional network structure that is formed by the metal ion and the ligand that is coordinated to the metal ion, and having pores and voids that are three-dimensionally arranged in the three-dimensional network structure in an ordered manner, at least one compound selected from the group consisting of an aliphatic hydrocarbon, an alicyclic hydrocarbon, an ether, an ester, an aromatic hydrocarbon, a halogenated hydrocarbon, and a nitrile being included in the pores and the voids as a guest compound (A), and the ratio of the amount of the guest compound (A) present in the pores and the voids to the total amount of the guest compound included in the pores and the voids being 60 mol % or more.

[2] The polymer-metal complex crystal including a guest compound according to [1], wherein the guest compound (A) is an alicyclic hydrocarbon having 3 to 20 carbon atoms or an aromatic hydrocarbon having 6 to 10 carbon atoms.

[3] The polymer-metal complex crystal including a guest compound according to [1] or [2], wherein the guest compound (A) is a saturated alicyclic hydrocarbon having 3 to 20 carbon atoms.

[4] The polymer-metal complex crystal including a guest compound according to any one of [1] to [3], wherein the total occupancy ratio of the guest compound included in the pores and the voids of the polymer-metal complex is 10% or more.

[5] The method for producing a crystal structure analysis sample according to any one of [1] to [4], wherein the ligand having two or more coordinating moieties is an organic ligand having three or more coordinating moieties, and the metal ion that serves as the center metal is a cobalt ion or a zinc ion.

[6] The polymer-metal complex crystal including a guest compound according to any one of [1] to [5], wherein the polymer-metal complex is a compound represented by $[[M(X)_2]_3(L)_2]_n$ (wherein M is a metal ion, X is a monovalent anion, L is a tridentate ligand represented by the following formula (1),

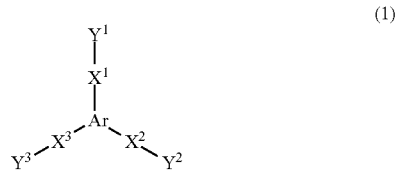

(1)

wherein Ar is a substituted or unsubstituted trivalent aromatic group, $X^1$ to $X^3$ are independently a divalent organic group, or a single bond that directly bonds Ar and $Y^1$, $Y^2$, or $Y^3$, and $Y^1$ to $Y^3$ are independently a monovalent organic group having a coordinating moiety, and n is an arbitrary natural number).

[7] The polymer-metal complex crystal including a guest compound according to any one of [1] to [6], wherein the metal ion is an ion of a metal among the metals that belong to Groups 8 to 12 in the periodic table.

[8] The polymer-metal complex crystal including a guest compound according to any one of [1] to [7], wherein the metal ion is a zinc(II) ion or a cobalt(II) ion.

[9] The polymer-metal complex crystal including a guest compound according to any one of [1] to [8], the polymer-metal complex crystal having a cubic or cuboidal shape with a side length of 10 to 1000 μm.

[10] A method for producing the polymer-metal complex crystal including a guest compound according to any one of [1] to [9], the method including immersing a polymer-metal complex crystal including a crystallization solvent in the guest compound (A) in a liquid state, or an inert solvent solution that includes the guest compound (A), the polymer-metal complex crystal including a crystallization solvent including a polymer-metal complex that includes a ligand having two or more coordinating moieties, and a metal ion that serves as a center metal, the polymer-metal complex having a three-dimensional network structure that is formed by the metal ion and the ligand that is coordinated to the metal ion, and having pores and voids that are three-dimensionally arranged in the three-dimensional network structure in an ordered manner, a crystallization solvent (excluding the guest compound (A)) being included in the pores and the voids.

[11] A method for preparing a crystal structure analysis sample in which a molecule of an organic compound for which a molecular structure is to be determined, is arranged in pores and voids of a polymer-metal complex crystal in an ordered manner, the method including:

immersing the polymer-metal complex crystal including a guest compound according to any one of [1] to [9] in a solvent solution that includes the organic compound.

[12] The method for preparing a crystal structure analysis sample according to [11], the method including immersing the polymer-metal complex crystal including a guest compound according to any one of [1] to [8] in the solvent solution that includes the organic compound in an amount of 100 μg or less so that a value A calculated by the following expression (2) is 0.1 to 30, $$A = \frac{b}{a} \quad (2)$$

where, b is the amount of the organic compound included in the solvent solution, and a is the amount of a substance having a specific gravity of 1 that is required to fill all of the pores and the voids of the polymer-metal complex crystal with the substance having a specific gravity of 1.

[13] The method for preparing a crystal structure analysis sample according to [11] or [12], wherein the concentration of the organic compound in the solvent solution is 0.001 to 50 μg/μL.

[14] The method for preparing a crystal structure analysis sample according to any one of [11] to [13], wherein the organic compound is impurities included in a compound derived from a natural product, or a synthetic compound.

[15] The method for preparing a crystal structure analysis sample according to any one of [11] to [14], the method including volatilizing the solvent after immersing the polymer-metal complex crystal including a guest compound in the solvent solution that includes the organic compound to concentrate the solvent solution.

[16] The method for preparing a crystal structure analysis sample according to [15], wherein the volatilization rate of the solvent is 0.1 to 1000 μL/24 hours.

[17] The method for preparing a crystal structure analysis sample according to [14] or [15], wherein the solvent is volatilized at 0 to 180° C.

[18] The method for preparing a crystal structure analysis sample according to any one of [11] to [17], wherein the immersing of the polymer-metal complex crystal including a guest compound in the solvent solution that includes the organic compound includes immersing one piece of the polymer-metal complex crystal including a guest compound in the solvent solution that includes the organic compound.

[19] The method for preparing a crystal structure analysis sample according to any one of [11] to [18], the method including:

a step (I) that separates a mixture that includes an organic compound for which a molecular structure is to be determined, by liquid chromatography to obtain a solvent solution of the organic compound for which the molecular structure is to be determined; and a step (II) that immerses the polymer-metal complex crystal including a guest compound according to any one of [1] to [8] in the solvent solution of the organic compound for which the molecular structure is to be determined, that has been obtained in the step (I), and volatilizes the solvent under moderate conditions to concentrate the solvent solution.

[20] The method for preparing a crystal structure analysis sample according to any one of [11] to [19], wherein the molecular structure of the resulting crystal structure analysis sample can be determined with a resolution of at least 1.5 Å by applying MoKα radiation (wavelength: 0.71 Å) generated at a tube voltage of 24 kV and a tube current of 50 mA to the crystal structure analysis sample, and detecting diffracted X-rays using a CCD detector.

[21] A method for determining the molecular structure of an organic compound including analyzing the crystal structure of a crystal structure analysis sample obtained using the method for preparing a crystal structure analysis sample according to any one of [11] to [20] to determine the molecular structure of the organic compound included in the pores and the voids of the crystal structure analysis sample.

Advantageous Effects of the Invention

The polymer-metal complex crystal including a guest compound according to one aspect of the invention makes it possible to prepare a crystal structure analysis sample that is useful for determining the molecular structure of a trace amount of organic compound.

The method for producing a polymer-metal complex crystal including a guest compound according to one aspect of the invention can efficiently produce the polymer-metal complex crystal including a guest compound according to one aspect of the invention.

The method for preparing a crystal structure analysis sample according to one aspect of the invention can easily and efficiently prepare a crystal structure analysis sample that makes it possible to determine the molecular structure of an organic compound even when the amount of the sample is very small.

The method for determining the molecular structure of an organic compound according to one aspect of the invention can determine the molecular structure of an organic compound even when the amount of sample is very small.

DESCRIPTION OF EMBODIMENTS

Figure 1:
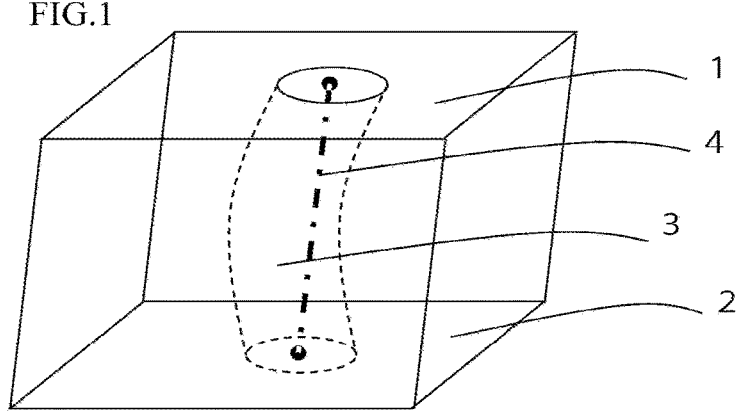
FIG. 1 is a view illustrating the extension direction of a pore formed in a polymer-metal complex.

A polymer-metal complex crystal including a guest compound, a method for producing a polymer-metal complex crystal including a guest compound, a method for preparing a crystal structure analysis sample, and a method for determining a molecular structure of an organic compound according to exemplary embodiments of the invention are described in detail below.

1) Polymer-Metal Complex Crystal Including Guest Compound

A polymer-metal complex crystal including a guest compound according to one embodiment of the invention includes a polymer-metal complex that includes a ligand having two or more coordinating moieties, and a metal ion that serves as a center metal, the polymer-metal complex having a three-dimensional network structure that is formed by the metal ion and the ligand that is coordinated to the metal ion, and having pores and voids (hereinafter may be referred to as "pores and the like") that are three-dimensionally arranged in the three-dimensional network structure in an ordered manner, at least one compound selected from the group consisting of an aliphatic hydrocarbon, an alicyclic hydrocarbon, an ether, an ester, an aromatic hydrocarbon, a halogenated hydrocarbon, and a nitrile being included in the pores and the voids as a guest compound (A), and the ratio of the amount of the guest compound (A) present in the pores and the voids to the total amount of the guest compound included in the pores and the voids being 60 mol % or more.

(i) Polymer-Metal Complex

The polymer-metal complex used in connection with the embodiments of the invention has a three-dimensional network structure that includes a ligand having two or more coordinating moieties, and a metal ion that serves as a center metal.

The term "three-dimensional network structure" used herein refers to a network-like structure in which a structural unit formed by a ligand (i.e., a ligand having two or more coordinating moieties and an additional monodentate ligand) and a metal ion that is bonded to the ligand is repeatedly arranged three-dimensionally.

Ligand

The ligand having two or more coordinating moieties (hereinafter may be referred to as "multidentate ligand") is not particularly limited as long as the ligand is coordinated to the metal ion to form the three-dimensional network structure. A known multidentate ligand may be used as the ligand having two or more coordinating moieties.

The term "coordinating moiety" used herein refers to an atom or an atomic group that is included in the ligand, and has an unshared electron pair that can form a coordination bond. Examples of the coordinating moiety include a hetero atom such as a nitrogen atom, an oxygen atom, a sulfur atom, and a phosphorus atom; an atomic group such as a nitro group, an amino group, a cyano group, and a carboxyl group; and the like. Among these, a nitrogen atom and an atomic group that includes a nitrogen atom are preferable.

It is preferable that the multidentate ligand include an aromatic ring since the planarity of the ligand is improved, and a strong three-dimensional network structure is easily formed.

It is preferable to use a multidentate ligand having two or more coordinating moieties, more preferably a multidentate ligand having three coordinating moieties (hereinafter may be referred to as "tridentate ligand"), and still more preferably a tridentate ligand in which the unshared electron pairs (orbitals) of the three coordinating moieties are present in the same plane, and the three coordinating moieties are arranged radially with respect to the center of the tridentate ligand at an equal interval.

The expression "present in the same plane" used herein includes a case where each unshared electron pair is present in the same plane, and a case where each unshared electron pair is present in a plane that is shifted to some extent (e.g., present in a plane that intersects a reference plane at an angle of 20° or less).

The expression "the three coordinating moieties are arranged radially with respect to the center of the tridentate ligand at an equal interval" used herein means that the three coordinating moieties are arranged on lines that extend radially from the center of the ligand at an equal interval, at an almost equal distance from the center of the ligand.

Examples of the tridentate ligand include a ligand represented by the following formula (1).

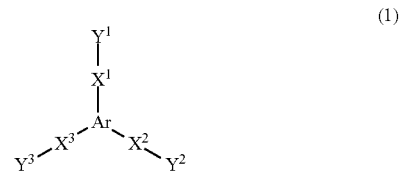

wherein Ar is a substituted or unsubstituted trivalent aromatic group, $X^1$ to $X^3$ are independently a divalent organic group, or a single bond that directly bonds Ar and $Y^1$, $Y^2$, or $Y^3$, and $Y^1$ to $Y^3$ are independently a monovalent organic group having a coordinating moiety.

Ar in the formula (1) is a trivalent aromatic group.

The number of carbon atoms of Ar is normally 3 to 22, preferably 3 to 13, and more preferably 3 to 6.

Examples of Ar include a trivalent aromatic group having a monocyclic structure that consists of one 6-membered aromatic ring, and a trivalent aromatic group having a fused ring structure in which three 6-membered aromatic rings are fused.

Examples of the trivalent aromatic group having a monocyclic structure that consists of one 6-membered aromatic ring include the groups respectively represented by the following formulas (2a) to (2d). Examples of the trivalent aromatic group having a fused ring structure in which three 6-membered aromatic rings are fused, include the group represented by the following formula (2e). Note that "*" in the formulas (2a) to (2e) indicates the positions at which $X^1$ to $X^3$ are bonded.

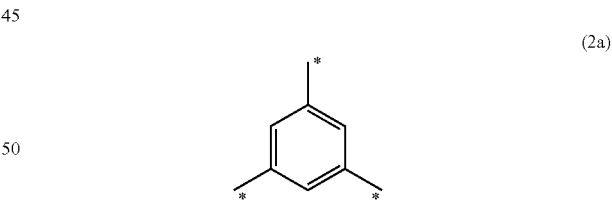

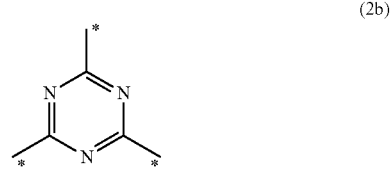

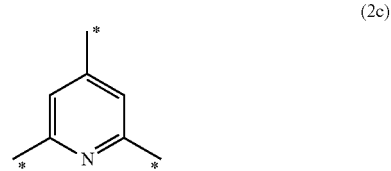

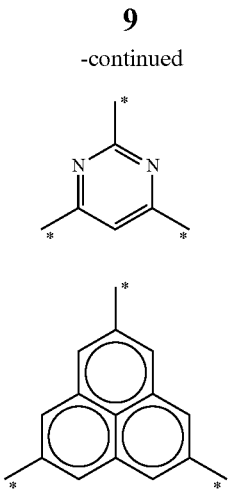

(2d)

(2e)

The aromatic groups represented by the formulas (2a) and (2c) to (2e) may be substituted with a substituent at an arbitrary position. Examples of a substituent include an alkyl group such as a methyl group, an ethyl group, an isopropyl group, an n-propyl group, and a t-butyl group; an alkoxy group such as a methoxy group, an ethoxy group, an n-propoxy group, and an n-butoxy group; a halogen atom such as a fluorine atom, a chlorine atom, and a bromine atom; and the like. Ar is preferably the aromatic group represented by the formula (2a) or (2b), and particularly preferably the aromatic group represented by the formula (2b).

$X^1$ to $X^3$ are independently a divalent organic group, or a single bond that directly bonds Ar and $Y^1$, $Y^2$, or $Y^3$.

The divalent organic group that may be represented by $X^1$ to $X^3$ is preferably a group that can form a pi electron conjugated system together with Ar. When the divalent organic group that may be represented by $X^1$ to $X^3$ forms a pi electron conjugated system, the planarity of the tridentate ligand represented by the formula (1) is improved, and a strong three-dimensional network structure is easily formed.

The number of carbon atoms of the divalent organic group is preferably 2 to 18, more preferably 2 to 12, and still more preferably 2 to 6.

Examples of the divalent organic group include a divalent unsaturated aliphatic group having 2 to 10 carbon atoms, a divalent organic group having a monocyclic structure that consists of one 6-membered aromatic ring, a divalent organic group having a fused ring structure in which two to four 6-membered aromatic rings are fused, an amide group (—C(=O)—NH—), an ester group (—C(=O)—O—), a combination of two or more divalent organic groups among these divalent organic groups, and the like.

Examples of the divalent unsaturated aliphatic group having 2 to 10 carbon atoms include a vinylene group, an acetylene group (ethynylene group), and the like.

Examples of the divalent organic group having a monocyclic structure that consists of one 6-membered aromatic ring, include a 1,4-phenylene group and the like.

Examples of the divalent organic group having a fused ring structure in which two to four 6-membered aromatic rings are fused, include a 1,4-naphthylene group, a 1,5-naphthylene group, a 2,6-naphthylene group, an anthracene-1,4-diyl group, and the like.

Examples of a combination of two or more divalent organic groups among these divalent organic groups include the groups respectively represented by the following formulas.

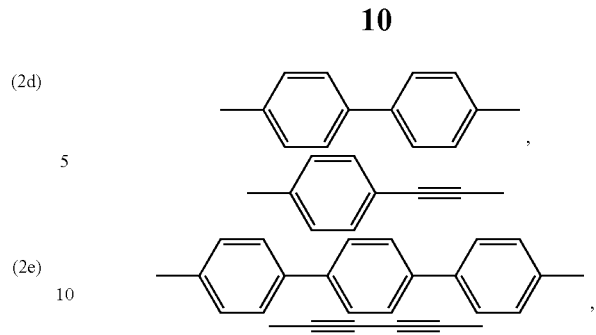

These aromatic rings may include a hetero atom such as a nitrogen atom, an oxygen atom, or a sulfur atom in their ring.

The divalent organic group may be substituted with a substituent. Examples of the substituent include those mentioned above in connection with Ar.

The groups respectively represented by the following formulas are preferable as the divalent organic group that may be represented by $X^1$ to $X^3$.

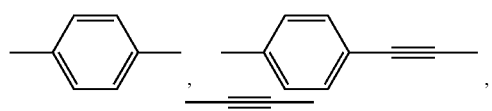

$Y^1$ to $Y^3$ are independently a monovalent organic group having a coordinating moiety.

The organic group represented by $Y^1$ to $Y^3$ is preferably a group that can form a pi electron conjugated system together with Ar and $X^1$ to $X^3$.

When the organic group represented by $Y^1$ to $Y^3$ forms a pi electron conjugated system, the planarity of the tridentate ligand represented by the formula (1) is improved, and a strong three-dimensional network structure is easily formed.

The number of carbon atoms of the organic group represented by $Y^1$ to $Y^3$ is preferably 5 to 11, and more preferably 5 to 7.

Examples of the organic group represented by $Y^1$ to $Y^3$ include the organic groups respectively represented by the following formulas (3a) to (3f). Note that "*" in the formulas (3a) to (3f) indicates the position at which $X^1$, $X^2$, or $X^3$ is bonded.

(3a)

(3b)

(3c) 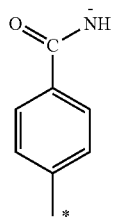

(3d) 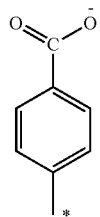

(3e) 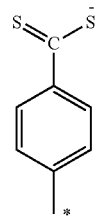

(3f) 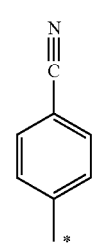

The organic groups represented by the formulas (3a) to (3f) may be substituted with a substituent at an arbitrary position. Examples of the substituent include those mentioned above in connection with Ar.

The group represented by the formula (3a) is particularly preferable as $Y^1$ to $Y^3$.

The size of the pores and the like of the polymer-metal complex can be adjusted by appropriately selecting Ar, $X^1$ to $X^3$, and $Y^1$ to $Y^3$ in the tridentate ligand represented by the formula (1). The method according to one embodiment of the invention makes it possible to efficiently obtain a single crystal of a polymer-metal complex that has pores and the like having a size sufficient to include an organic compound for which the molecular structure is to be determined.

It is preferable that the tridentate ligand represented by the formula (1) have high planarity and high symmetry, and have a structure in which a pi-conjugated system extends over the entire ligand, since a strong three-dimensional network structure is easily formed. Examples of such a tridentate ligand include the ligands respectively represented by the following formulas (4a) to (4f).

(4a) 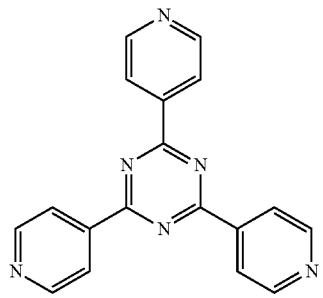

(4b) 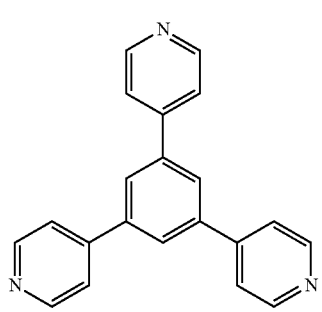

(4c) 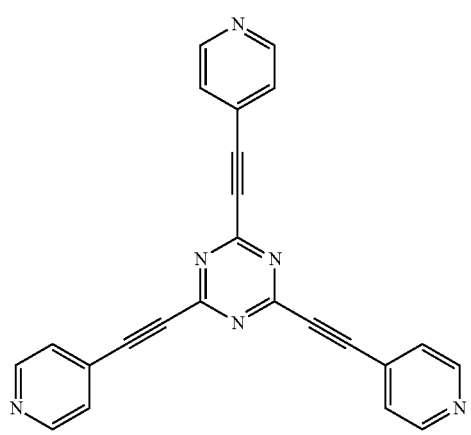

(4d) 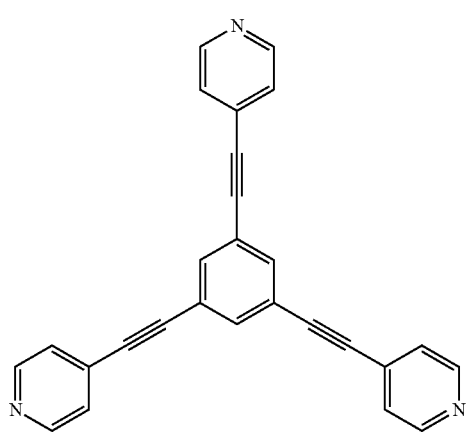

(4e)

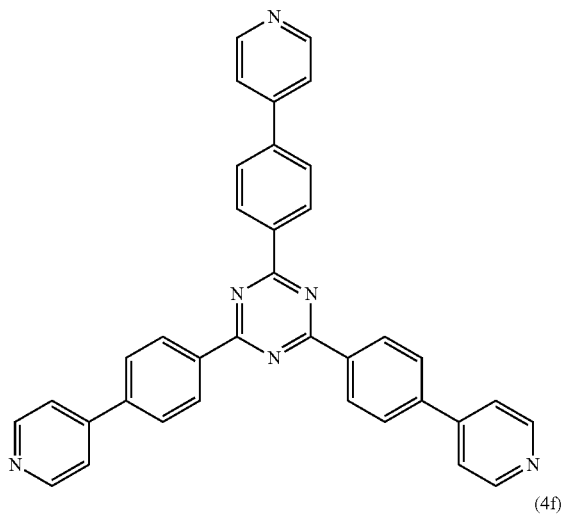

(4f)

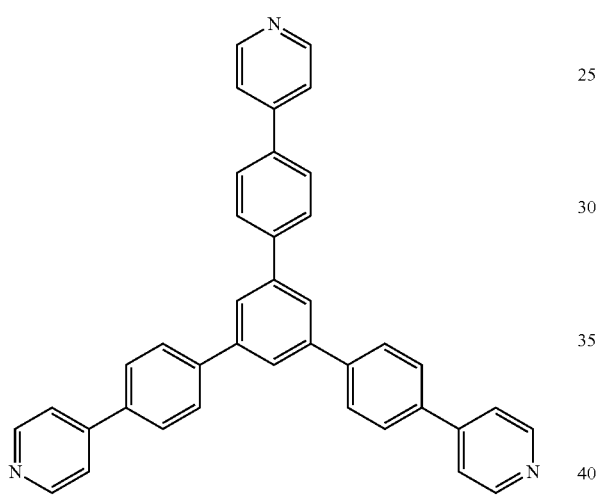

Among these, 2,4,6-tris(4-pyridyl)-1,3,5-triazine (TPT) represented by the formula (4a) is particularly preferable as the tridentate ligand represented by the formula (1).

Metal Ion

The metal ion that serves as the center metal is not particularly limited as long as the metal ion forms a coordination bond together with the multidentate ligand to form the three-dimensional network structure. A known metal ion may be used as the metal ion that serves as the center metal. It is preferable to use an ion of a metal among the metals that belong to Groups 8 to 12 in the periodic table, such as an iron ion, a cobalt ion, a nickel ion, a copper ion, a zinc ion, or a silver ion, and more preferably an ion of a divalent metal among the metals that belong to Groups 8 to 12 in the periodic table. It is particularly preferable to use a zinc(II) ion or a cobalt(II) ion, since a polymer-metal complex having large pores and the like can be easily obtained.

Additional Component Included in Polymer-Metal Complex

The polymer-metal complex used in connection with the embodiments of the invention is normally stabilized due to coordination of a monodentate ligand that serves as a counter ion in addition to the neutral multidentate ligand.

Examples of the monodentate ligand include a monovalent anion such as a chloride ion ($Cl^-$), a bromide ion ($Br^-$), an iodide ion (I–), and a thiocyanate ion ($SCN^-$).

The polymer-metal complex used in connection with the embodiments of the invention may include a solvent; an electrically neutral coordinating compound such as ammonia, a monoalkylamine, a dialkylamine, a trialkylamine, and ethylenediamine; a framework-forming aromatic compound (described below); and the like.

The term "framework-forming aromatic compound" used herein refers to an aromatic compound that is restrained within the three-dimensional network structure due to a bond (other than a coordination bond) or interaction, and forms part of the framework of a host molecule (i.e., a compound in which a guest compound can be incorporated). When the polymer-metal complex includes the framework-forming aromatic compound, the three-dimensional network structure easily becomes stronger, and may be further stabilized even in a state in which the polymer-metal complex includes the molecule of an organic compound for which the molecular structure is to be determined.

Examples of the framework-forming aromatic compound include a fused polycyclic aromatic compound. Examples of the fused polycyclic aromatic compound include the compounds respectively represented by the following formulas (5a) to (5i).

(5a)

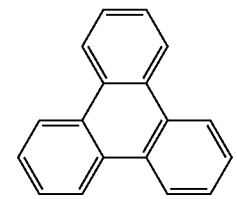

(5b)

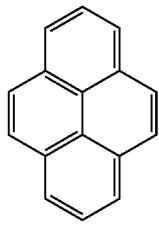

(5c)

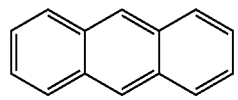

(5d)

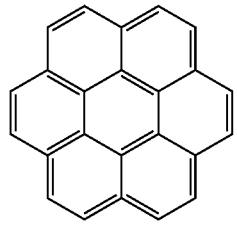

(5e)

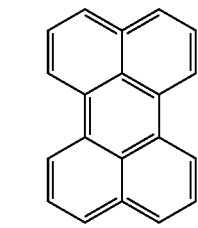

(5f)

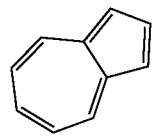

(5g)

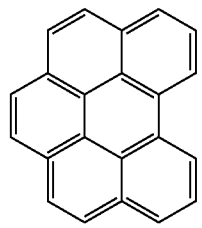

(5h)

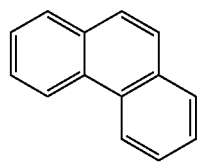

(5i)

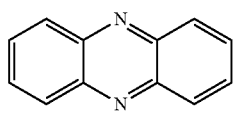

Three-Dimensional Network Structure of Polymer-Metal Complex

The polymer-metal complex used in connection with the embodiments of the invention has the three-dimensional network structure that is formed by the metal ion and the multidentate ligand that is coordinated to the metal ion, and has the pores and the like that are three-dimensionally arranged in the three-dimensional network structure in an ordered manner.

The expression "the pores and the like that are three-dimensionally arranged in the three-dimensional network structure in an ordered manner" means that the pores and the like are arranged in the three-dimensional network structure in an ordered manner to such an extent that the pores and the like can be observed by X-ray single crystal structure analysis.

Figure 3:
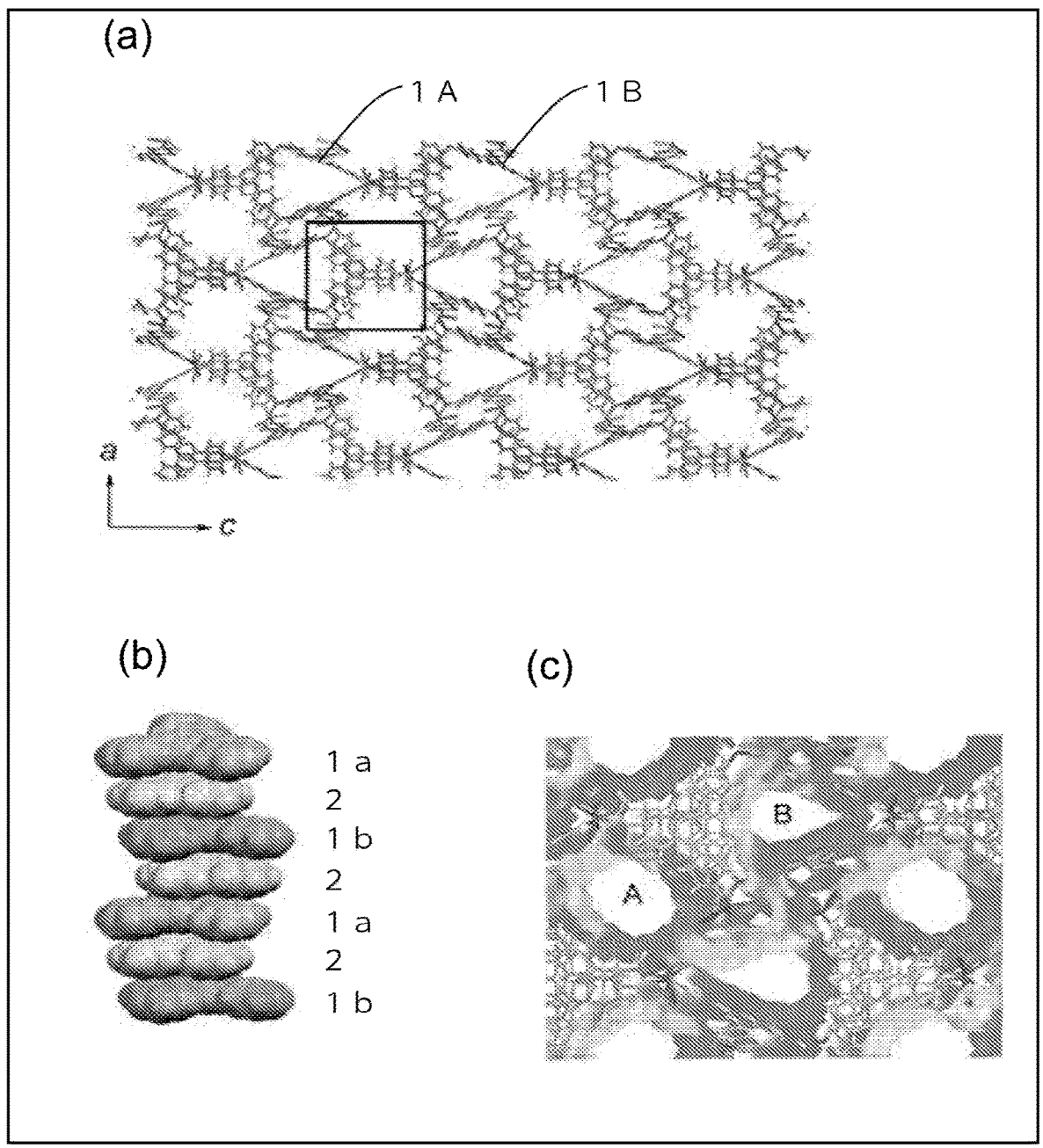
FIG. 3 is a view illustrating the three-dimensional network structure of the polymer-metal complex 3.
Figure 4:
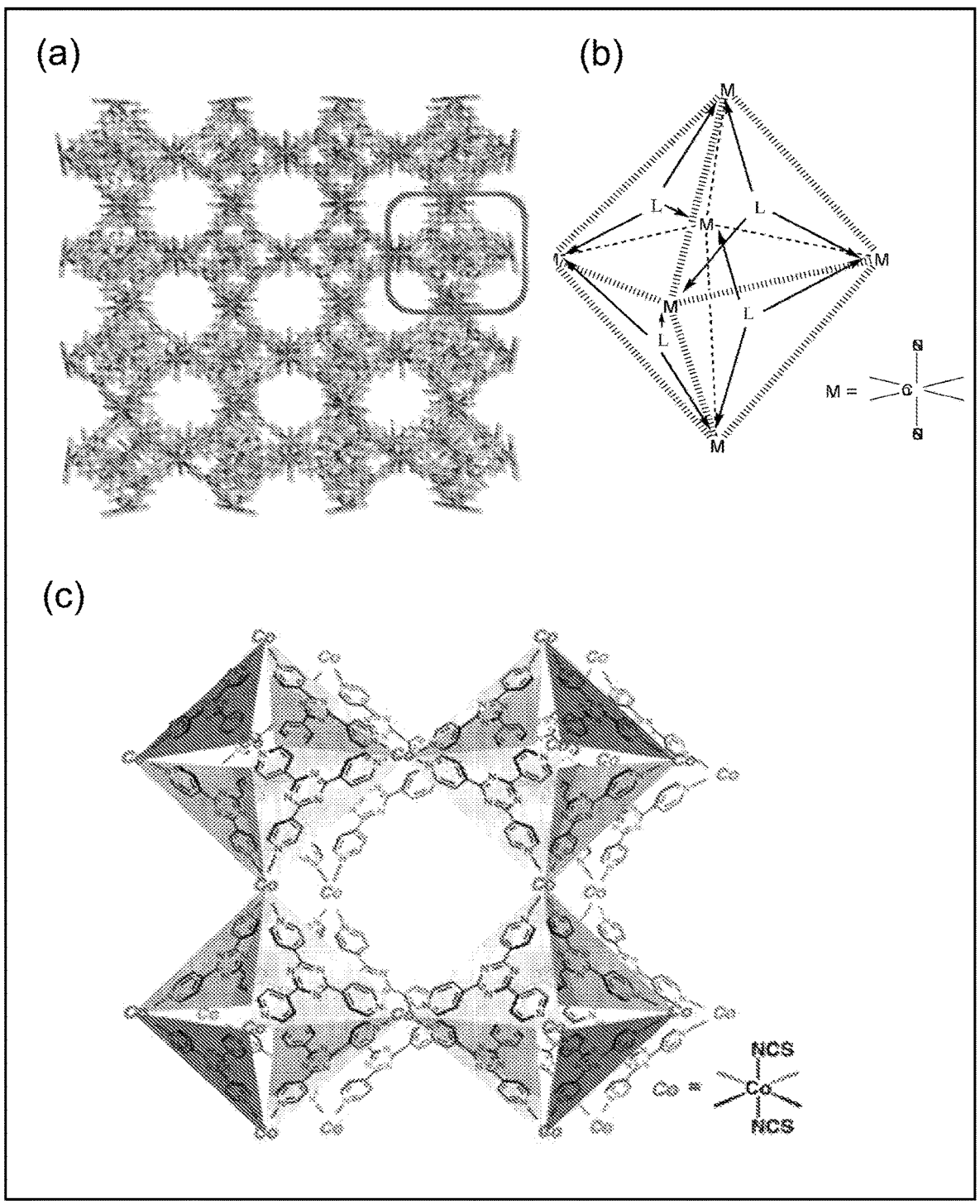
FIG. 4 is a view illustrating the three-dimensional network structure of the polymer-metal complex 5.

The term "pore" used herein refers to a space defined by the three-dimensional network structure of the polymer-metal complex, such as spaces A and B (see (a) and (b) in FIG. 3) that are defined by the three-dimensional network structure, and a space (white area) (see (a) in FIG. 4) that is formed between the repeating units of the spherical complex structure (purple area). The term "void" used herein refers to an internal space of the spherical complex structure, such as the repeating unit (an area enclosed by the red line (see (b) in FIG. 4) of the spherical complex structure (see (a) in FIG. 4).

Note that the expressions "pores formed in the three-dimensional network structure", "pores of the polymer-metal complex", and "pores formed in the single crystal" used herein have the same meaning.

The three-dimensional network structure is not particularly limited as long as the three-dimensional network structure has the above structural features, and the pores and the like have a size sufficient to include the molecule of an organic compound for which the molecular structure is to be determined.

A polymer-metal complex having relatively large pores and the like is normally obtained when a multidentate ligand is used in which the distance from the center of the ligand to the coordinating moiety is long, and a polymer-metal complex having relatively small pores and the like is normally obtained when a multidentate ligand is used in which the distance from the center of the ligand to the coordinating moiety is short.

The size of the pore has a correlation with the diameter of a circle that is inscribed to the pore (hereinafter may be referred to as "pore inscribed circle") in a plane parallel to the crystal plane that is closest to a perpendicular plane with respect to the extension direction of the pore (hereinafter may be referred to as "parallel plane").

The extension direction of the pore may be determined by the following method.

Specifically, a crystal plane X (e.g., plane A, plane B, plane C, or diagonal plane thereof) in an appropriate direction that intersects the target pore is selected. The atoms that are present in the crystal plane X and included in the host molecule are represented using the van der Waals radius to draw a cross-sectional view of the pore taken along the crystal plane X. Likewise, a cross-sectional view of the pore taken along a crystal plane Y that is shifted from the crystal plane X by one unit cell is drawn. The center of the cross-sectional shape of the pore in the crystal plane X and the center of the cross-sectional shape of the pore in the crystal plane Y are connected using a straight line (dash-dotted line) (see FIG. 1). The direction of the straight line corresponds to the extension direction of the pore.

The diameter of the pore inscribed circle may be determined by the following method.

Specifically, a cross-sectional view of the pore taken along the parallel plane is drawn in the same manner as described above. The pore inscribed circle is drawn using the cross-sectional view, and the diameter of the pore inscribed circle is measured. The measured value is converted into the actual scale to determine the actual diameter of the pore inscribed circle.

The diameter of the pore inscribed circle in each parallel plane is measured while gradually shifting the parallel plane in parallel by one unit cell to determine the diameter of the smallest inscribed circle and the diameter of the largest inscribed circle.

The diameter of the pore inscribed circle of the polymer-metal complex used in connection with the embodiments of the invention is preferably 2 to 30 Å, and more preferably 3 to 10 Å.

When the shape of the pore significantly differs from a true circle, it is preferable to predict the guest molecule inclusion capability of the polymer-metal complex from the minor axis and the major axis of the pore inscribed ellipse in the parallel plane.

The major axis of the pore inscribed ellipse of the polymer-metal complex used in connection with the embodiments of the invention is preferably 2 to 30 Å, and more preferably 3 to 10 Å. The minor axis of the pore inscribed ellipse of the polymer-metal complex used in connection with the embodiments of the invention is preferably 2 to 30 Å, and more preferably 3 to 10 Å.

The pore volume in the polymer-metal complex used in connection with the embodiments of the invention may be calculated using the method described in Acta Crystallogr. A46, 194-201 (1990). Specifically, the pore volume in the polymer-metal complex may be calculated using the expression "volume of single crystal×void ratio in unit cell" based on the solvent accessible void (void volume in unit cell) calculated by a calculation program "PLATON SQUEEZE PROGRAM".

The pore volume (i.e., the total pore volume in one piece of the single crystal) in the polymer-metal complex used in connection with the embodiments of the invention is preferably $1\times10^{-7}$ to 0.1 mm$^3$, and more preferably $1\times10^{-5}$ to $1\times10^{-3}$ mm$^3$.

When the polymer-metal complex includes the repeating units of the spherical complex structure, each spherical complex structure has an internal space (void). The size of the void may be calculated using the method described in Acta Crystallogr. A46, 194-201 (1990) in the same manner as the pore volume.

It is preferable that the polymer-metal complex used in connection with the embodiments of the invention does not lose crystallinity, and have relatively large pores and the like even after the guest compound has been introduced into (incorporated in) the pores and the like.

The polymer-metal complex includes an organic solvent (hereinafter may be referred to as "crystallization solvent") used when synthesizing the polymer-metal complex in the pores and the like.

When the crystallization solvent is the guest compound (A), the resulting polymer-metal complex corresponds to the polymer-metal complex including a guest compound according to one embodiment of the invention.

When the crystallization solvent is not the guest compound (A), the crystallization solvent is replaced with the guest compound (A) as described later to obtain a polymer-metal complex including a guest compound that may suitably be used to prepare a crystal structure analysis sample.

The polymer-metal complex used in connection with the embodiments of the invention is normally obtained by mixing a first solvent solution of the ligand having two or more coordinating moieties and a second solvent solution that includes a metal salt so that the resulting polymer-metal complex includes the ligand and the metal ion in a given ratio. For example, the tridentate ligand represented by the formula (1) may be used as the ligand, and a zinc(II) salt such as zinc iodide or zinc bromide, a cobalt(II) salt such as cobalt thiocyanate, or the like may be used as the metal salt. Note that the details of the method for synthesizing the polymer-metal complex are described later.

Specific examples of the polymer-metal complex used in connection with the embodiments of the invention include polymer-metal complexes respectively represented by the following formulas (6a) to (6d) that are obtained using TPT respectively by the formula (4a) as the tridentate ligand. These polymer-metal complexes are particularly suitable as the polymer-metal complex used in connection with the embodiments of the invention.

  (6a)

  (6b)

  (6c)

  (6d)

wherein "solv" is the crystallization solvent included in the pores and the like, "SA" is the framework-forming aromatic compound, and a and b are an arbitrary natural number.

These polymer-metal complexes are described in detail below. Note that the ligand and the solvent molecule may be hereinafter abbreviated as shown below.

PhNO$_2$: nitrobenzene
TPH: triphenylene
PER: perylene
MeOH: methanol
DCB: 1,2-dichlorobenzene

  (6a)

Examples of the polymer-metal complex represented by the formula (6a) include [(ZnI$_2$)$_3$(TPT)$_2$(PhNO$_2$)$_{5.5}$]$_n$ (polymer-metal complex 1) disclosed in JP-A-2008-214584 and J. Am. Chem. Soc. 2004, v. 126, pp. 16292-16293.

Figure 2:
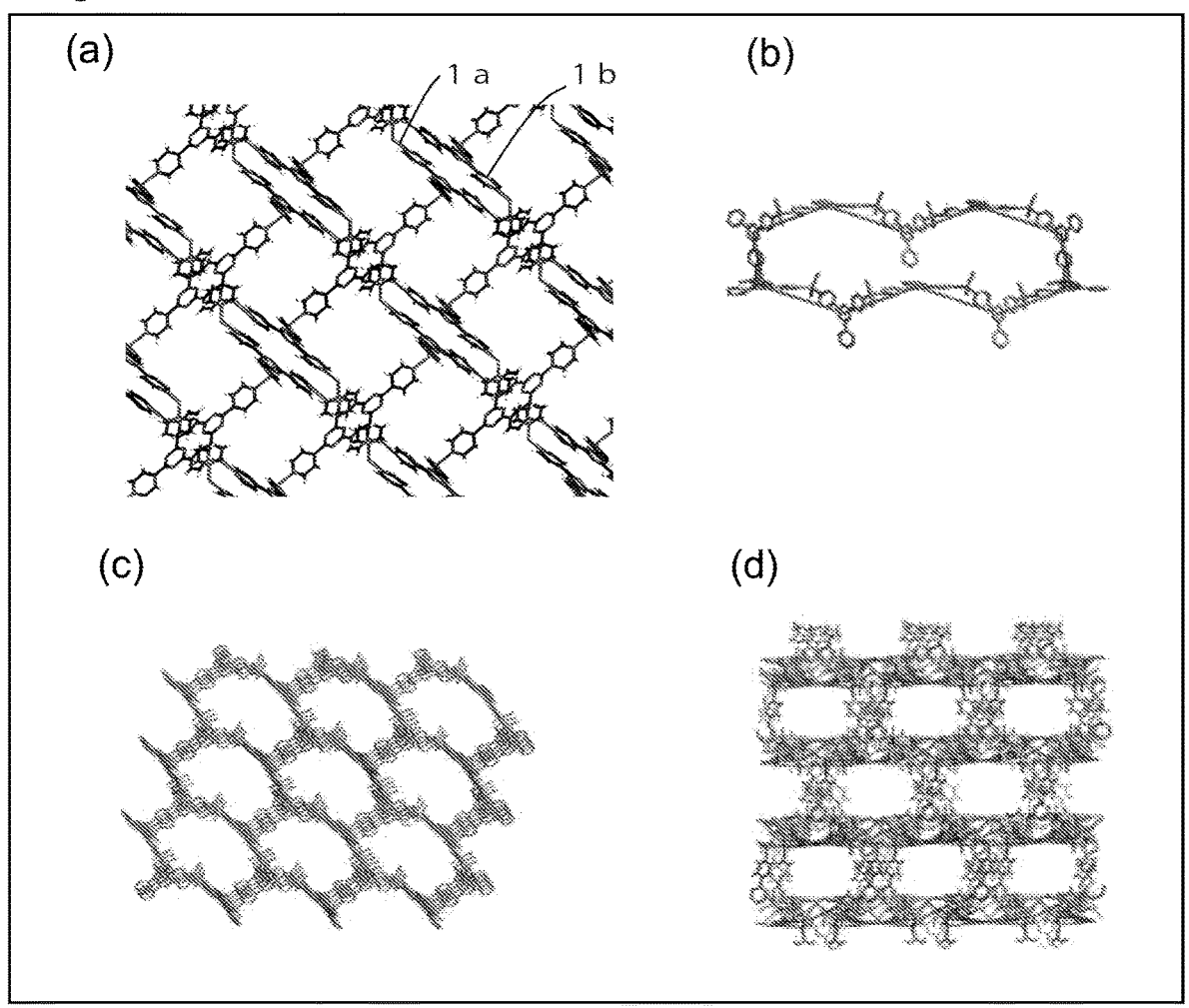
FIG. 2 is a view illustrating the three-dimensional network structure of the polymer-metal complex 1.

FIG. 2 (see (a) to (d)) illustrates the three-dimensional network structure of the polymer-metal complex 1.

The three-dimensional network structure of the polymer-metal complex 1 includes three-dimensional network structures 1a and 1b. In the three-dimensional network structures 1a and 1b, the pyridyl groups of two TPT and two iodide ions are coordinated to each zinc(II) ion to form a tetra-coordinated tetrahedral structure. The structures including the zinc(II) ion are three-dimensionally connected by TPT to form each three-dimensional network structure (see (a) in FIG. 2).

The three-dimensional network structures 1a and 1b have a closed cyclic chain structure that consists of ten TPT molecules and ten Zn atoms as the shortest closed cyclic chain structure (see (b) in FIG. 2).

The three-dimensional network structures 1a and 1b are considered to be a helical hexagonal three-dimensional network structure in which the pitch along the (010) axis is 15 Å (see (c) in FIG. 2).

The three-dimensional network structures 1a and 1b do not share an identical zinc(II) ion, and are independent of each other. The three-dimensional network structures 1a and 1b penetrate each other in a complex nested form so as to share an identical space to form a composite three-dimensional network structure.

The polymer-metal complex 1 having the composite three-dimensional network structure has identical pores that are arranged in an ordered manner (see (d) in FIG. 2).

The void ratio of the polymer-metal complex 1 is 50%.
The diameter of the pore inscribed circle of the polymer-metal complex 1 is 5 to 8 Å.

  (6b)

Examples of the polymer-metal complex represented by the formula (6b) include [(ZnBr$_2$)$_3$(TPT)$_2$(PhNO$_2$)$_5$(H$_2$O)]$_n$ (polymer-metal complex 2) disclosed in JP-A-2008-214318.

The polymer-metal complex 2 has the same three-dimensional network structure as that of the polymer-metal complex 1, except that (ZnI$_2$) is replaced with (ZnBr$_2$).

The pore shape, the pore size, and the void ratio of the polymer-metal complex 2 are almost the same as those of the polymer-metal complex 1.

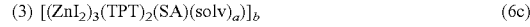  (6c)

Examples of the polymer-metal complex represented by the formula (6c) include [(ZnI$_2$)$_3$(TPT)$_2$(TPH)(PhNO$_2$)$_{3.9}$ (MeOH)$_{1.8}$]$_n$ (polymer-metal complex 3) and [(ZnI$_2$)$_3$ (TPT)$_2$(PER)(PhNO$_2$)$_4$]$_n$ (polymer-metal complex 4) disclosed in JP-A-2006-188560.

FIG. 3 (see (a) to (c)) illustrates the three-dimensional network structure of the polymer-metal complex 3.

The three-dimensional network structure of the polymer-metal complex 3 includes three-dimensional network structures 1A and 1B. In the three-dimensional network structures 1A and 1A, two iodide ions and the pyridyl groups of two TPT are coordinated to each zinc(II) ion to form a tetra-coordinated tetrahedral structure. The structures including the zinc(II) ion are three-dimensionally connected by TPT to form each three-dimensional network structure.

The three-dimensional network structures 1A and 1B do not share an identical zinc(II) ion, and are independent of each other. The three-dimensional network structures 1A and 1B penetrate each other in a complex nested form so as to share an identical space to form a composite three-dimensional network structure.

The triphenylene molecule (2) included in the polymer-metal complex 3 is firmly intercalated between the pi plane of tris(4-pyridyl)triazine (TPT (1a)) of the three-dimensional network structure 1A and the pi plane of tris(4-pyridyl) triazine (TPT (1b)) of the three-dimensional network structure 1B (see (b) in FIG. 3). The triphenylene molecule is stabilized by the pi-pi interaction between TPT (1a) and TPT (1b), and serves as part of the main framework of the polymer-metal complex 3. In FIG. 3, (b) is a side view of the area enclosed in (a).

The polymer-metal complex 3 has two types of pores (pores A and B) that are arranged in the three-dimensional network structure in an ordered manner (see (c) in FIG. 3). The pores A and B are formed in an ordered manner in a laminate structure in which TPT and TPH are alternately stacked.

The pore A has an approximately cylindrical shape, and is almost completely surrounded by the hydrogen atoms present at the side edge of the pi planes of a number of TPT and TPH that are stacked.

The pore B is approximately in the shape of a triangular prism. Two sides among the three sides of the triangular prism are surrounded by the pi planes of TPT, and the remaining side is surrounded by the hydrogen atoms present at the side edge of the pi planes of a number of TPT and TPH that are stacked.

The pores A and B have an elongated shape that meanders to some extent.

The void ratio of the polymer-metal complex 3 is 28%.

The diameter of the circle inscribed to the pore A of the polymer-metal complex 3 is 5 to 8 Å.

The diameter of the circle inscribed to the pore B of the polymer-metal complex 3 is 5 to 8 Å.

The polymer-metal complex 4 has the same framework structure as that of the polymer-metal complex 3, except that the perylene molecule is intercalated between two TPT instead of the triphenylene molecule.

The pore shape, the pore size, and the void ratio of the polymer-metal complex 4 are almost the same as those of the polymer-metal complex 3.

(4) $[(Co(NCS)_2)_3(TPT)_4(solv)_a]_b$ (6d)

Examples of the polymer-metal complex represented by the formula (6d) include $[(Co(NCS)_2)_3(TPT)_4(DCB)_{25}(MeOH)_5]_n$ (polymer-metal complex 5) disclosed in WO2011/062260.

FIG. 4 (see (a)) illustrates the three-dimensional network structure of the polymer-metal complex 5.

The polymer-metal complex 5 has a $(Co_6(TPT)_4)$ structure that consists of six cobalt ions and four TPT as a structural unit. The structural unit has an octahedral shape, wherein a cobalt ion is situated at each vertex of the octahedron (see (b) in FIG. 4). The pyridyl groups of four TPT and two thiocyanate ions are coordinated to each cobalt(II) ion to form a hexa-coordinated octahedral structure. In FIG. 4, (b) is an enlarged view of the area enclosed in (a).

The $(Co_6(TPT)_4)$ structure are three-dimensionally connected so as to share the cobalt ion situated at each vertex of the $(Co_6(TPT)_4)$ structure to form pores between the $(Co_6(TPT)_4)$ structures (see (c) in FIG. 4).

The structural unit has a void therein.

The void ratio of the polymer-metal complex 5 is 78%. This value is calculated using the total volume of the pores and the like.

The diameter of the pore inscribed circle of the polymer-metal complex 5 is 10 to 18 Å.

It is preferable that the polymer-metal complex crystal including a guest compound according to one embodiment of the invention does not hinder introduction (incorporation) of the desired organic compound into the pores and the like, and be designed so that the guest compound (A) included in the pores and the like is replaced with the desired organic compound to form a polymer-metal complex crystal including an organic compound.

At least one compound selected from the group consisting of an aliphatic hydrocarbon, an alicyclic hydrocarbon, an ether, an ester, an aromatic hydrocarbon, a halogenated hydrocarbon, and a nitrile is preferable as the guest compound (A) from the above point of view.

The aliphatic hydrocarbon that may be used as the guest compound (A) is not particularly limited as long as the aliphatic hydrocarbon can enter the pores and the like. Examples of the aliphatic hydrocarbon that may be used as the guest compound (A) include a linear or branched saturated aliphatic hydrocarbon having 1 to 20 carbon atoms, such as methane, ethane, propane, butane, pentane, hexane, heptane, octane, decane, tetradecane, and octadecane; a linear or branched unsaturated aliphatic hydrocarbon having 2 to 20 carbon atoms that includes one or two or more double bonds or triple bonds in the molecule; and the like.

The alicyclic hydrocarbon is not particularly limited as long as the alicyclic hydrocarbon can enter the pores and the like. Examples of the alicyclic hydrocarbon include a saturated alicyclic hydrocarbon having 3 to 20 carbon atoms, such as cyclopropane, cyclobutane, cyclopentane, cyclohexane, cycloheptane, cyclooctane, cyclononane, cyclodecane, cyclododecane, cycloundecane, and decalin; an unsaturated alicyclic hydrocarbon having 3 to 20 carbon atoms that is derived from these compounds, and has one or two or more double bonds or triple bonds in the molecule; and the like.

The ether is not particularly limited as long as the ether can enter the pores and the like. Examples of the ether include dimethyl ether, diethyl ether, dipropyl ether, dibutyl ether, t-butyl ether, dihexyl ether, methylethyl ether, tetrahydrofuran, 1,2-dimethoxyethane, 1,4-dioxane, and the like.

The ester is not particularly limited as long as the ester can enter the pores and the like. Examples of the ester include ethyl formate, methyl acetate, ethyl acetate, propyl acetate, pentyl acetate, octyl acetate, ethyl lactate, ethyl propionate, methyl butanoate, ethyl butanoate, pentyl butanoate, pentyl valerate, and the like.

The aromatic hydrocarbon is not particularly limited as long as the aromatic hydrocarbon can enter the pores and the like. Examples of the aromatic hydrocarbon include benzene, toluene, xylene, mesitylene, naphthalene, anthracene, phenanthrene, and the like.

The halogenated hydrocarbon is not particularly limited as long as the halogenated hydrocarbon can enter the pores and the like. Examples of the halogenated hydrocarbon include the compounds mentioned above in connection with the aliphatic hydrocarbon, the alicyclic hydrocarbon, and the aromatic hydrocarbon, in which one or two or more carbon atoms are substituted with a halogen atom such as a fluorine atom, a chlorine atom, a bromine atom, or an iodine atom.

Specific examples of the halogenated hydrocarbon include dichloromethane, chloroform, carbon tetrachloride, 1,2-dichloroethane, trifluoromethane, chlorobenzene, bromobenzene, 1,2-dichlorobenzene, and the like.

The nitrile is not particularly limited as long as the nitrile can enter the pores and the like. Examples of the nitrile include acetonitrile, benzonitrile, and the like.

These compounds may be used either alone or in combination.

Among these, an alicyclic hydrocarbon having 3 to 20 carbon atoms and an aromatic hydrocarbon having 6 to 10 carbon atoms are preferable, an alicyclic hydrocarbon having 5 to 10 carbon atoms and an aromatic hydrocarbon having 6 to 10 carbon atoms are more preferable, cyclohexane and toluene are still more preferable, and cyclohexane is particularly preferable, since replacement with an organic compound can be easily achieved, and a high-quality crystal structure analysis sample can be easily prepared.

The ratio of the amount of the guest compound (A) present in the polymer-metal complex to the total amount of the guest compound included in the pores and the like is 60 mol % or more, preferably 75 mol % or more, and more preferably 90 mol % or more.

If the ratio of the amount of the guest compound (A) present in the polymer-metal complex to the total amount of the guest compound included in the pores and the like is less than 60 mol %, it may be difficult to easily prepare the target crystal structure analysis sample.

In the polymer-metal complex crystal including a guest compound according to one embodiment of the invention, the total occupancy ratio of the guest compound included in the pores and the voids of the polymer-metal complex is preferably 10% or more, more preferably 30% or more, and still more preferably 50% or more.

If the occupancy ratio is less than 10%, it may be impossible or very difficult to determine the structure of the guest compound by X-ray single crystal structure analysis, and the resulting structural data may have low chemical reliability.

The term "occupancy ratio" used herein refers to a value obtained by single crystal structure analysis, and represents the amount of guest compound actually present in the single crystal provided that the amount of guest compound in an ideal inclusion state is 100%.

2) Method for Producing Polymer-Metal Complex Crystal Including Guest Compound

A method for producing a polymer-metal complex crystal including a guest compound (hereinafter may be referred to as "production method") according to one embodiment of the invention includes immersing a polymer-metal complex crystal including a crystallization solvent in the guest compound (A) in a liquid state, or an inert solvent solution that includes the guest compound (A), the polymer-metal complex crystal including a crystallization solvent including a polymer-metal complex that includes a ligand having two or more coordinating moieties, and a metal ion that serves as a center metal, the polymer-metal complex having a three-dimensional network structure that is formed by the metal ion and the ligand that is coordinated to the metal ion, and having pores and the like that are three-dimensionally arranged in the three-dimensional network structure in an ordered manner, a crystallization solvent (excluding the guest compound (A), hereinafter the same) being included in the pores and the like.

Specifically, the production method according to one embodiment of the invention includes (i) synthesizing a polymer-metal complex crystal in a crystallization solvent to obtain a polymer-metal complex crystal including a crystallization solvent, and (ii) immersing the polymer-metal complex crystal including the crystallization solvent in the guest compound (A) in a liquid state, or an inert solvent solution that includes the guest compound (A), to replace the crystallization solvent included in the pores and the like with the guest compound (A).

(i) Synthesis of Polymer-Metal Complex Crystal Including Crystallization Solvent The polymer-metal complex including a crystallization solvent used in connection with one embodiment of the invention may be synthesized using a known method that reacts a multidentate ligand and a metal ion-containing compound, for example. For example, the polymer-metal complex including a crystallization solvent may be synthesized by adding a second solvent solution of a metal ion-containing compound to a first solvent solution of a multidentate ligand, and allowing the mixture to stand at 0 to 70° C. for several hours to several days.

The metal ion-containing compound is not particularly limited. Examples of the metal ion-containing compound include a compound represented by $MX_n$. Note that M is a metal ion, X is a counter ion, and n is the valence of M.

Specific examples of X include $F^-$, $Cl^-$, $Br^-$, $I^-$, $SCN^-$, $NO_3^-$, $ClO_4^-$, $BF_4^-$, $SbF_4^-$, $PF_6^-$, $AsF_6^-$, $CH_3CO_2^-$, and the like.

It is preferable to use a compound that dissolves the multidentate ligand or the like as the first solvent and the second solvent.

Specific examples of such a compound include an aromatic hydrocarbon such as benzene, toluene, xylene, chlorobenzene, 1,2-dichlorobenzene, and nitrobenzene; an aliphatic hydrocarbon such as n-pentane, n-hexane, and n-heptane; an alicyclic hydrocarbon such as cyclopentane, cyclohexane, and cycloheptane; a nitrile such as acetonitrile and benzonitrile; a sulfoxide such as dimethyl sulfoxide (DMSO); an amide such as N,N-dimethylformamide and N-methylpyrrolidone; an ether such as diethyl ether, tetrahydrofuran, 1,2-dimethoxyethane, and 1,4-dioxane; an alcohol such as methanol, ethanol, and isopropyl alcohol; a ketone such as acetone, methyl ethyl ketone, and cyclohexanone; a cellosolve such as ethylcellosolve; a halogenated hydrocarbon such as dichloromethane, chloroform, carbon tetrachloride, and 1,2-dichloroethane; an ester such as methyl acetate, ethyl acetate, ethyl lactate, and ethyl propionate; water; and the like. These solvents may be used either alone or in combination.

When it is desired to obtain a relatively large single crystal of the polymer-metal complex, it is preferable that the first solvent and the second solvent be immiscible with each other (i.e., be separated into two layers). Specifically, it is preferable to use nitrobenzene, dichlorobenzene, nitrobenzene, or a mixed solvent thereof with methanol as the first solvent, and use an alcohol such as methanol, ethanol, or isopropyl alcohol as the second solvent.

The polymer-metal complexes 1 to 5 can be synthesized using the methods described in the above documents.

(ii) Replacement with Guest Compound

The resulting polymer-metal complex has a three-dimensional network structure, and has pores and the like that are three-dimensionally arranged in the three-dimensional network structure in an ordered manner, and the crystallization solvent is included in the pores and the like.

The target polymer-metal complex crystal including a guest compound can be obtained by immersing the polymer-metal complex crystal including a crystallization solvent in the guest compound (A) in a liquid state, or an inert solvent solution that includes the guest compound (A), to replace the crystallization solvent included in the pores and the like with the guest compound (A).

Examples of the guest compound (A) include those mentioned above.

The inert solvent is not particularly limited as long as the inert solvent is miscible with the guest compound (A), and inert to the polymer-metal complex (i.e., does not easily replace the crystallization solvent included in the pores and the like of the polymer-metal complex as compared with the guest compound (A)). Examples of the inert solvent include an alcohol such as methanol, ethanol, and isopropyl alcohol.

When the guest compound (A) is liquid, the guest compound (A) may be used directly.

The guest compound (A) in a liquid state, or the inert solvent solution that includes the guest compound (A) (hereinafter may be referred to as "solution of the guest compound (A)") is normally used in an amount of 1 to 100 mL, and preferably 5 to 30 mL, based on 100 mg of the polymer-metal complex crystal.

The immersion temperature is not particularly limited, but is normally 0 to 70° C., preferably 10 to 70° C., and more preferably 20 to 60° C.

The immersion time is determined so that 60% or more of the pores and the like are occupied by the guest compound (A). The immersion time is normally 6 hours or more, preferably 12 hours to 10 days, and more preferably 1 to 8 days.

It is preferable to remove the supernatant liquid of the immersion liquid (i.e., the solution of the guest compound (A)) by decantation about every other day, and add the immersion liquid in amount equal to the amount of the supernatant liquid that has been removed, in order to promote replacement with the guest compound (A).

Whether or not the guest compound (A) is included in the pores and the like may be determined by elemental analysis, X-ray crystal structure analysis, and the like.

Since the polymer-metal complex crystal including a guest compound obtained as described above is designed so that the guest compound (A) included in the pores and the like is easily replaced with a trace amount of organic compound sample, the polymer-metal complex crystal including a guest compound is useful as a material for preparing a crystal structure analysis sample described later.

The polymer-metal complex crystal including a guest compound obtained as described above makes it possible to efficiently introduce (incorporate) various other guest compounds without hindering guest replacement. The sample used for guest replacement need not be a crystalline solid, and may be a liquid, a gas, a noncrystalline solid, or the like. The amount of the guest compound necessary for inclusion may be 5 µg or less. Good X-ray single crystal structure analysis data can be obtained even when the amount of the guest compound is several tens of nanograms. X-ray single crystal structure analysis that utilizes the embodiments of the invention can accurately determine a steric structure including the absolute configuration of a molecule. It is also possible to determine the steric structure (absolute structure) of an unstable compound that easily undergoes thermal decomposition or solvolysis without heating the compound, or dissolving the compound in a solvent, a buffer, or the like.

It is preferable that the polymer-metal complex crystal including a guest compound according to one embodiment of the invention be a single crystal having a cubic or cuboidal shape with a side length of 10 to 1000 µm, and preferably 60 to 200 µm. A high-quality crystal structure analysis sample can be easily obtained by utilizing the single crystal of the polymer-metal complex having such a shape.

It is preferable that the single crystal of the polymer-metal complex including a guest compound according to one embodiment of the invention be designed so that the molecular structure of the resulting crystal structure analysis sample can be determined with a resolution of at least 1.5 Å by applying MoKα radiation (wavelength: 0.71 Å) generated at a tube voltage of 24 kV and a tube current of 50 mA to the crystal structure analysis sample, and detecting diffracted X-rays using a CCD detector. A high-quality crystal structure analysis sample can be obtained by utilizing the single crystal of the polymer-metal complex having the above properties.

3) Method for Producing Crystal Structure Analysis Sample

A method for preparing a crystal structure analysis sample according to one embodiment of the invention prepares a crystal structure analysis sample in which the molecules of an organic compound for which the molecular structure is to be determined, are arranged in pores and the like of a polymer-metal complex crystal in an ordered manner, and includes immersing the polymer-metal complex crystal including a guest compound according to one embodiment of the invention in a solvent solution that includes the organic compound.

Organic Compound for which Molecular Structure is Determined

The organic compound for which the molecular structure is to be determined (hereinafter may be referred to as "organic compound (a)") is not particularly limited as long as the organic compound has a size that allows the organic compound to enter the pores and the like of the polymer-metal complex.

The organic compound (a) is a low-molecular-weight compound, the molecular weight of the organic compound (a) is normally 20 to 3000, and preferably 100 to 500.

When the organic compound (a) is a chain-like polymer compound (e.g., polyethylene) that includes a repeating unit, the molecular weight of the organic compound (a) is normally $10^3$ to $10^6$, and preferably $10^4$ to $10^5$. The organic compound (a) may be either solid or liquid at about room temperature (about 25° C.).

It is preferable to roughly determine the size of the organic compound (a) in advance by nuclear magnetic resonance spectroscopy, mass spectrometry, elemental analysis, or the like, and appropriately select the polymer-metal complex crystal including a guest compound corresponding to the size of the organic compound (a).

When the organic compound (a) is impurities included in a synthetic compound (e.g., a compound derived from a natural product, agricultural chemical, medicine, or synthetic polymer), it is preferable to increase the purity of the organic compound (a) using a known purification method such as liquid chromatography, and then prepare the crystal structure analysis sample using the method according to one embodiment of the invention. When using liquid chromatography, the eluant that includes the target product may be used directly as the solvent solution of the organic compound described later.

The method for preparing a crystal structure analysis sample according to one embodiment of the invention can prepare the crystal structure analysis sample without requiring a large amount of the organic compound (α), and is useful when only a trace amount of the organic compound (α) is available (e.g., when the organic compound (α) is impurities included in a compound derived from a natural product, an agricultural chemical, or a medicine). The organic compound (α) may be either solid or liquid at room temperature (20° C.).

The amount of the organic compound (α) included in the solvent solution is not particularly limited, and may be 100 μg or less. The lower limit of the amount of the organic compound (α) included in the solvent solution is normally 0.5 μg or more.

It is preferable that the method for preparing a crystal structure analysis sample according to one embodiment of the invention include immersing the single crystal of the polymer-metal complex including a guest compound in the solvent solution that includes the organic compound in an amount of 100 μg or less so that a value A calculated by the following expression (2) is 100 or less, preferably 0.1 to 30, and more preferably 1 to 5.

$$A = \frac{b}{a} \qquad (2)$$

where, b is the amount of the organic compound included in the solvent solution, and a is the amount of a substance having a specific gravity of 1 that is required to fill all of the pores and the like of the polymer-metal complex crystal with the substance having a specific gravity of 1.

When the value A is 0.1 to 30, the organic compound (α) is sufficiently introduced into the pores and the like of the single crystal of the polymer-metal complex, and a high-quality crystal structure analysis sample is easily obtained. The target crystal structure analysis sample can be obtained even when the value A is large. However, a further improvement in effects may not be achieved, and the organic compound (α) may be wasted. Specifically, the method according to one embodiment of the invention is useful when preparing a crystal structure analysis sample for determining the structure of an organic compound that is available in an only trace amount (e.g., impurities included in a compound derived from a natural product, an agricultural chemical, or a medicine).

Note that the organic compound (α) need not necessarily be included in all of the pores and the likes of the polymer-metal complex. It is possible to prepare a high-quality crystal structure analysis sample even when the value A is smaller than 1.

The concentration of the organic compound (α) in the solvent solution is not particularly limited. The concentration of the organic compound (α) in the solvent solution is normally 0.001 to 50 μg/μL, preferably 0.01 to 5 μg/μL, and more preferably 0.1 to 1 μg/μL, from the viewpoint of efficiently preparing a high-quality crystal structure analysis sample.

The solvent used to prepare the solvent solution is not particularly limited as long as the solvent does not dissolve the crystal of the polymer-metal complex, and dissolves the organic compound (α), and the solvent solution of the organic compound (α) can be concentrated by volatilizing the solvent from the solvent solution of the organic compound (α).

It is preferable to use a solvent having a boiling point at normal pressure ($1 \times 10^5$ Pa) of 0 to 250° C., more preferably 0 to 185° C., and still more preferably 30 to 150° C.

Specific examples of the solvent include an aromatic hydrocarbon such as benzene, toluene, xylene, chlorobenzene, and 1,2-dichlorobenzene; an aliphatic hydrocarbon such as n-pentane, n-hexane, and n-heptane; an alicyclic hydrocarbon such as cyclopentane, cyclohexane, and cycloheptane; a nitrile such as acetonitrile and benzonitrile; a sulfoxide such as dimethyl sulfoxide; an amide such as N,N-dimethylformamide and N-methylpyrrolidone; an ether such as diethyl ether, tetrahydrofuran, 1,2-dimethoxyethane, and 1,4-dioxane; an alcohol such as methanol, ethanol, and isopropyl alcohol; a ketone such as acetone, methyl ethyl ketone, and cyclohexanone; a cellosolve such as ethylcellosolve; a halogenated hydrocarbon such as dichloromethane, chloroform, carbon tetrachloride, and 1,2-dichloroethane; an ester such as methyl acetate, ethyl acetate, ethyl lactate, and ethyl propionate; water; and the like. These solvents may be used either alone or in combination.

It is preferable to use the guest compound (A) as the solvent since a high-quality crystal structure analysis sample can be obtained.

When implementing the method for preparing a crystal structure analysis sample according to one embodiment of the invention, the polymer-metal complex crystal including a guest compound according to one embodiment of the invention is immersed in the solvent solution that includes the organic compound (α).

The number of single crystals of the polymer-metal complex including a guest compound to be immersed in the solvent solution is not particularly limited as long as the requirement relating to the value A is satisfied. When the amount of the organic compound (α) is very small, the target crystal structure analysis sample can be obtained by immersing one single crystal. When the amount of the organic compound (α) is large, two or more single crystals of an identical polymer-metal complex including a guest compound may be immersed in the solvent solution, or single crystals of different polymer-metal complexes including a guest compound may be immersed in the solvent solution at the same time.

When implementing the method for preparing a crystal structure analysis sample according to one embodiment of the invention, the solvent is volatilized under moderate conditions after immersing the single crystal of the polymer-metal complex including a guest compound in the solvent solution to concentrate the solvent solution. This makes it possible to efficiently introduce a trace amount of the organic compound (α) into the pores and the like of the single crystal.

The immersion conditions (concentration conditions) are not particularly limited. The temperature of the solvent is preferably 0 to 180° C., more preferably 0 to 80° C., and still more preferably 20 to 60° C.

The immersion time (concentration time) is normally 6 hours or more, preferably 12 to 168 hours, and more preferably 24 to 78 hours.

The volatilization rate of the solvent is preferably 0.1 to 1000 μL/24 hours, more preferably 1 to 100 μL/24 hours, and still more preferably 5 to 50 μL/24 hours.

If the volatilization rate of the solvent is to high, it may be difficult to obtain a high-quality crystal structure analysis sample. If the volatilization rate of the solvent is to low, the work efficiency may deteriorate.

The temperature employed when volatilizing the solvent is determined taking account of the boiling point of the organic solvent, but is normally 0 to 180° C., preferably 0 to 120° C., and more preferably 15 to 60° C.

The operation that volatilizes the solvent after immersing the polymer-metal complex crystal including a guest compound in the solvent solution that includes the organic compound (α) to concentrate the solvent solution may be performed under normal pressure, or may be performed under reduced pressure, or may be performed under pressure.

The pressure employed when performing the operation that volatilizes the solvent to concentrate the solvent solution is normally 1 to $1\times10^6$ Pa, and preferably to $1\times10$ to $1\times10^6$ Pa.

The volatilization rate of the solvent can be appropriately adjusted by adjusting the temperature and the pressure employed when performing the operation that concentrates the solvent solution.

The method for preparing a crystal structure analysis sample according to one embodiment of the invention may include a step (I) that separates a mixture that includes the organic compound ($\alpha$) by liquid chromatography to obtain a solvent solution of the organic compound ($\alpha$), and a step (II) that immerses the single crystal of the polymer-metal complex including a guest compound in the solvent solution of the organic compound ($\alpha$) that has been obtained in the step (I), and volatilizes the solvent under moderate conditions to concentrate the solvent solution.

Figure 26:
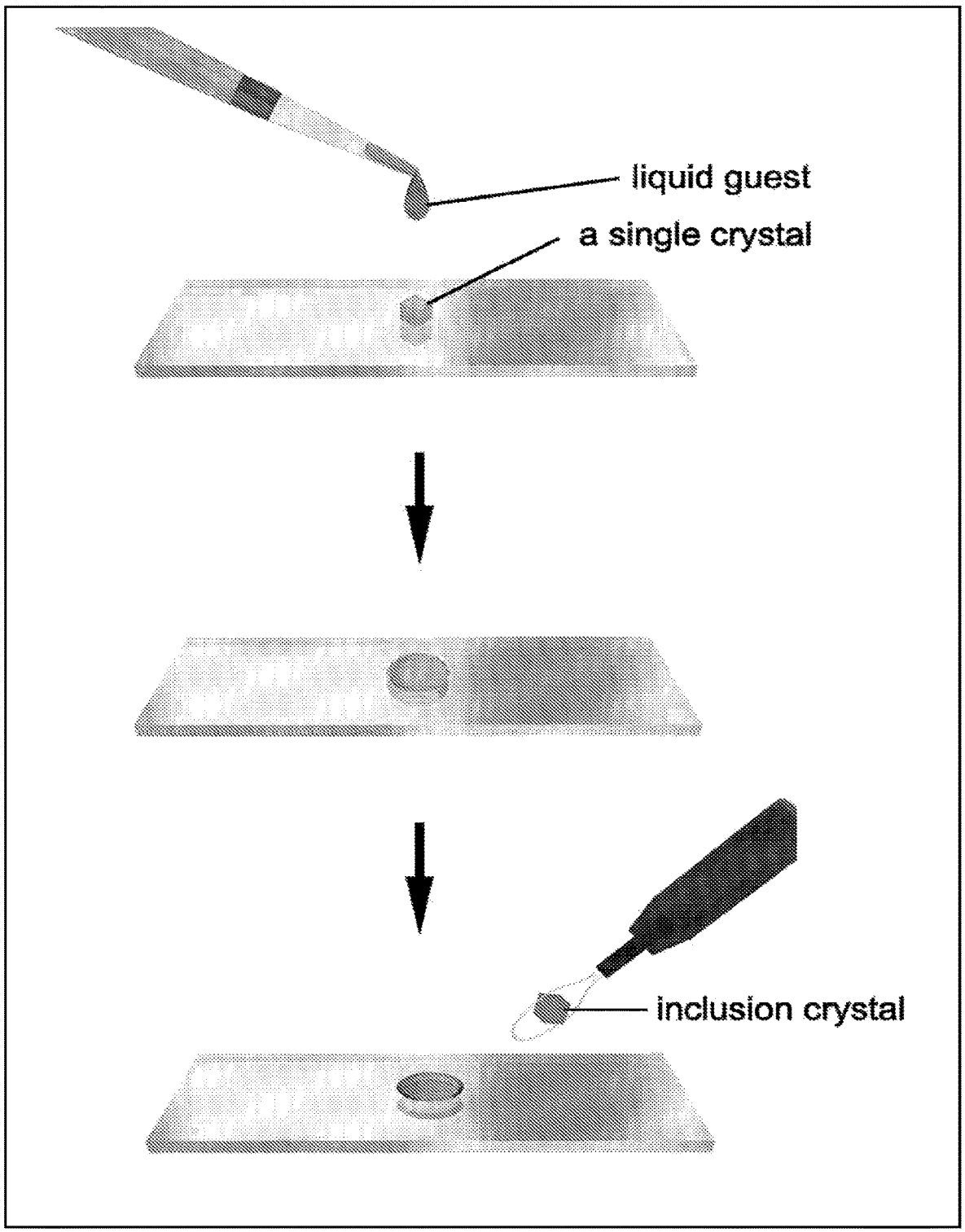
FIG. 26 is a schematic view illustrating an operation that drops an organic compound (liquid) for which the molecular structure is to be determined, onto a single crystal of a polymer-metal complex including a guest compound using a dropper to prepare a crystal structure analysis sample.

As illustrated in FIG. 26, a mixture that includes the organic compound ($\alpha$) is separated using a liquid chromatography device to obtain a solvent solution of the organic compound ($\alpha$) (i.e., a solution that includes the organic compound ($\alpha$) as an organic compound other than the solvent), the single crystal of the polymer-metal complex including a guest compound according to one embodiment of the invention is immersed in the solvent solution of the organic compound ($\alpha$) (fraction A), and the solvent is volatilized under moderate conditions to concentrate the solvent solution to obtain a crystal structure analysis sample.

In this case, the solvent of the solvent solution may be replaced with another solvent, and the crystal of the polymer complex may be immersed in the resulting solution.

According to this method, a crystal structure analysis sample can be prepared by separating a mixture of a plurality of compounds having a similar structure by liquid chromatography, and immersing the crystal of the polymer-metal complex in each of the solvent solutions respectively including the separated compounds. This method is useful when separating a mixture of compounds having a similar structure for which it is difficult to determine the structure of each compound based only on the measurement data (e.g., NMR spectrum), and determining the molecular structure of each compound.

The method for preparing a crystal structure analysis sample according to one embodiment of the invention can also be applied the case where the organic compound ($\alpha$) is a substance that is liquid at about room temperature (about 25° C.). Specifically, the single crystal of the polymer-metal complex including a guest compound according to one embodiment of the invention is immersed in the solvent solution of a liquid organic compound ($\alpha$), and the solvent is volatilized under moderate conditions to concentrate the solvent solution to prepare a crystal structure analysis sample.

As illustrated in FIG. 26, a trace amount of a liquid organic compound ($\alpha$) may be dropped onto the single crystal of the polymer-metal complex including a guest compound according to one embodiment of the invention using a dropper or the like, and the single crystal may be allowed to stand at room temperature (25° C.) for several hours to several days to prepare a crystal structure analysis sample. When the organic compound ($\alpha$) is volatile at about room temperature (25° C.), it is preferable to place the sample obtained by dropping the organic compound ($\alpha$) onto the single crystal of the polymer-metal complex including a guest compound in an airtight container such as a vial.

It is preferable that the molecular structure of the resulting crystal structure analysis sample (single crystal of a polymer-metal complex including an organic compound) can be determined with a resolution of at least 1.5 Å by applying MoK$\alpha$ radiation (wavelength: 0.71 Å) generated at a tube voltage of 24 kV and a tube current of 50 mA to the crystal structure analysis sample, and detecting diffracted X-rays using a CCD detector.

A crystal structure analysis sample obtained using the method according to one embodiment of the invention has a configuration in which the molecules of the organic compound ($\alpha$) that has replaced the guest compound (A) are arranged in the pores and the like of the single crystal of the polymer-metal complex in an ordered manner.

The expression "the molecules of the organic compound are arranged in an ordered manner" means that the molecules of the organic compound are included in the pores and the like of the polymer-metal complex in an ordered manner to such an extent that the structure of the organic compound can be determined by X-ray single crystal structure analysis.

In the crystal structure analysis sample obtained using the method according to one embodiment of the invention, the organic compound ($\alpha$) need not necessarily be included in all of the pores and the like of the single crystal of the polymer-metal complex as long as the structure of the organic compound ($\alpha$) can be determined. For example, the solvent used for the solvent solution of the organic compound ($\alpha$) may be included in some of the pores and the like of the single crystal of the polymer-metal complex.

It is preferable that the occupancy ratio of the molecules of the organic compound in the crystal structure analysis sample obtained using the method according to one embodiment of the invention be 10% or more. The occupancy ratio of the molecules of the organic compound refers to a value obtained by single crystal structure analysis, and represents the amount of guest molecules actually present in the single crystal provided that the amount of guest molecules (organic compound ($\alpha$)) in an ideal inclusion state is 100%.

It is possible to efficiently prepare a crystal structure analysis sample by satisfying the requirement relating to the value A, selecting the crystal of the polymer-metal complex having pores and the like that are appropriate for the size of the molecule of the organic compound ($\alpha$), and introducing the organic compound ($\alpha$) into the pores and the like of the single crystal of the polymer-metal complex having good quality.

Figure 5:
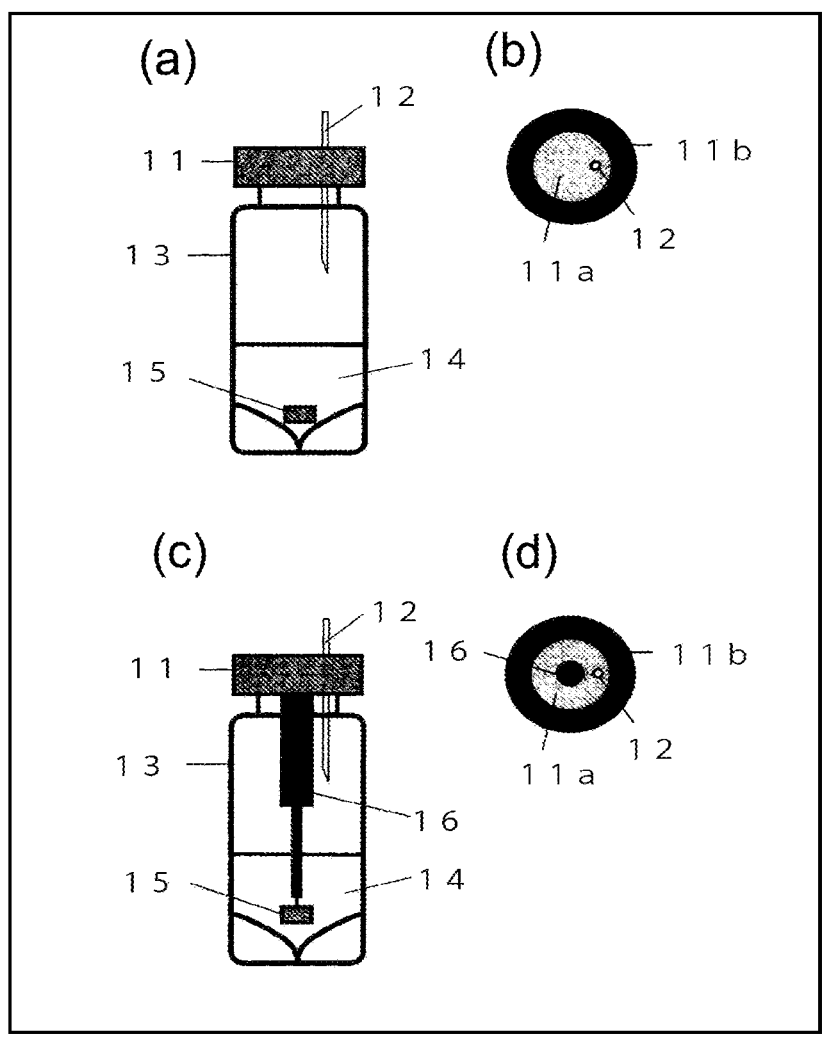
FIG. 5 is a view illustrating an example of a device used when concentrating a solvent solution.

When volatilizing the solvent after immersing the single crystal of the polymer-metal complex including a guest compound in the solvent solution of the organic compound ($\alpha$) to concentrate the solvent solution, the preparation device A or the preparation device B illustrated in FIG. 5 may be used, for example.

In FIG. 5, (a) is a side view illustrating the preparation device A, and (b) is a top view illustrating the preparation device A.

Reference sign 11 indicates a cap, reference sign 12 indicates an opening that allow gaseous molecules to pass through, reference sign 13 indicates a container main body, reference sign 14 indicates a solvent solution of the organic compound ($\alpha$), and reference sign 15 indicates a single crystal of a polymer-metal complex.

The cap (11) is not particularly limited as long as the container can be closed air-tightly. For example, a cap made of rubber (e.g., septum) may be used as the cap (11). The opening (12) may be formed by inserting a degassing hollow needle into the cap (11), for example. A container made of glass (e.g., test tube or pressure-resistant glass bottle) may be used as the container main body (13), for example. The bottom of the container main body (13) may be flat. Note that it is preferable that the bottom of the container main body (13) have a pointed shape (see (a) in FIG. 5) since the crystal can be easily placed and removed (i.e., excellent operability is achieved). When a transparent container is used as the container main body (13), it is possible to easily observe the volatilization state of the solvent and a change in color of the crystal (i.e., the color of the crystal changes when the guest molecules are introduced into the pores and the voids of the polymer-metal complex) from the outside.

When using the preparation device A illustrated in FIG. 5 (see (a) and (b)), the solvent included in the solvent solution (14) of the organic compound (α) gradually volatilizes through the thin opening (12) (degassing hollow needle), and is completely removed from the organic compound (α). After opening the cap (11) (sealing plug), the crystal structure analysis sample is removed from the container main body (vial) (13), and crystal structure analysis is performed using the crystal structure analysis sample.

In FIG. 5, (c) is a side view illustrating the preparation device B, and (d) is a top view illustrating the preparation device B.

As illustrated in FIG. 5 (see (c) and (d)), the preparation device B includes an airtight container that includes a cap (11), a container main body (13), and an opening (12) that allow gaseous molecules to pass through, and a crystal support (16) that is secured on the cap, and is configured so that a single crystal (15) of a polymer-metal complex that includes a ligand having two or more coordinating moieties, and a metal ion that serves as a center metal, and has a three-dimensional network structure can be secured on the front end of the crystal support (16), and the front end of the crystal support (16) is situated downward inside the container when the container is closed.

The preparation device B illustrated in FIG. 5 (see (c)) is configured so that the single crystal (15) of the polymer-metal complex is secured on the front end of the crystal support (16) using a cryoloop (not illustrated in FIG. 5).

It is preferable that the preparation device B be configured so that it is possible to introduce the organic compound (α) into the pores and the voids of the polymer-metal complex to obtain a crystal structure analysis sample, and transfer the crystal structure analysis sample directly to a crystal structure analyzer such as an X-ray crystal structure analyzer to perform measurement.

4) Method for Determining Molecular Structure of Organic Compound

A method for determining the molecular structure of an organic compound according to one embodiment of the invention includes analyzing the crystal structure of a crystal structure analysis sample obtained using the method for preparing a crystal structure analysis sample according to one embodiment of the invention to determine the molecular structure of the organic compound included in the pores and the voids of the crystal structure analysis sample.

The method for determining the molecular structure of an organic compound according to one embodiment of the invention may utilize X-ray diffraction or neutron diffraction.

When determining the molecular structure of the organic compound using the method for determining the molecular structure of an organic compound according to one embodiment of the invention, a known method may be used, except that the crystal structure analysis sample obtained using the method for preparing a crystal structure analysis sample according to one embodiment of the invention is mounted instead of a known single crystal.

The method for determining the molecular structure of an organic compound according to one aspect of the invention can efficiently analyze the crystal structure of an organic compound, and determine the molecular structure of the organic compound even when the amount of the organic compound is very small.

The method for determining the molecular structure of an organic compound according to one aspect of the invention can determine the molecular structure of an organic compound that is liquid at room temperature by utilizing the crystal structure analysis sample that includes the organic compound.

The organic compound used to prepare the sample may be a gas, a liquid, or a solid. The organic compound can be introduced into the single crystal of the polymer-metal complex as long as the organic compound can be dissolved in an organic solvent.

The amount of the organic compound required for one piece of the single crystal of the polymer-metal complex may be 5 µg or less. A single crystal structure can be obtained even when the amount of the organic compound is 50 ng.

It is possible to promptly and accurately determine the structure of a trace amount of impurities, essence, and food additive included in a medicine, a trace component included in animals and plants, and the like by utilizing the method for determining the molecular structure of an organic compound according to one embodiment of the invention. It is also possible to determine the steric structure (absolute structure) of an unstable compound that easily undergoes thermal decomposition or solvolysis without heating the compound, or dissolving the compound in a solvent, a buffer, or the like.

EXAMPLES

The invention is further described below by way of examples. Note that the invention is not limited to the following examples.
Equipment
(1) X-Ray Single Crystal Structure Analysis X-ray single crystal structure analysis was performed using an APEX II/CCD diffractometer (manufactured by Bruker, radiation source: Mo-Kα radiation (wavelength: 0.71 Å), output: 50 mA, 24 kV).
(2) Elemental Analysis Elemental analysis was performed using an analyzer "MT-6" (manufactured by YANACO).

Example 1: Synthesis of Polymer-Metal Complex Crystal Including Cyclohexane

Step 1: Synthesis of Polymer-Metal Complex Crystal Including Crystalline Solvent (Nitrobenzene)

50.2 mg (0.16 mmol) of 2,4,6-tris(4-pyridyl)-1,3,5-triazine (TPT) was dissolved in a nitrobenzene/methanol (32 mL/4 mL) mixture to prepare a ligand solution. A metal solution prepared by dissolving 76.5 mg (0.24 mmol) of $ZnI_2$ in 8 mL of methanol was mixed with the ligand solution at room temperature. The mixture was stirred for 30 seconds, and a precipitate (white crystals) was filtered off to obtain 151.7 mg of a white powder (yield: 81.6%).

The resulting white powdery sample was identified by elemental analysis and thermogravimetry-mass spectrometry (TG-MS), and found to be $[(ZnI_2)_3(TPT)_2(PhNO_2)_{5.5}]_n$ (polymer-metal complex 1).

Elemental Analysis Results
　Cald.: C: 36.68%, H: 2.30%, N: 10.85%.
　Found: C: 36.39%, H: 2.43%, N: 10.57%.

Step 2: Synthesis of Polymer-Metal Complex Crystal Including Guest Molecule (Cyclohexane)

The polymer-metal complex 1 (polymer-metal complex crystal including nitrobenzene) obtained in the step 1 was immersed in cyclohexane in a ratio of 100 mg/10 mL. The mixture was heated to 45° C. using an incubator, and allowed to stand for 1 week. The supernatant liquid (cyclohexane) was exchanged by decantation every other day during this period.

When 1 week had elapsed, the single crystal was removed, and identified by elemental analysis and crystal structure analysis. It was found that the single crystal was $[(ZnI_2)_3(TPT)_2(cyclohexane)_4]$.

The elemental analysis results are shown below. Table 1 shows the crystallographic data.

Figure 6:
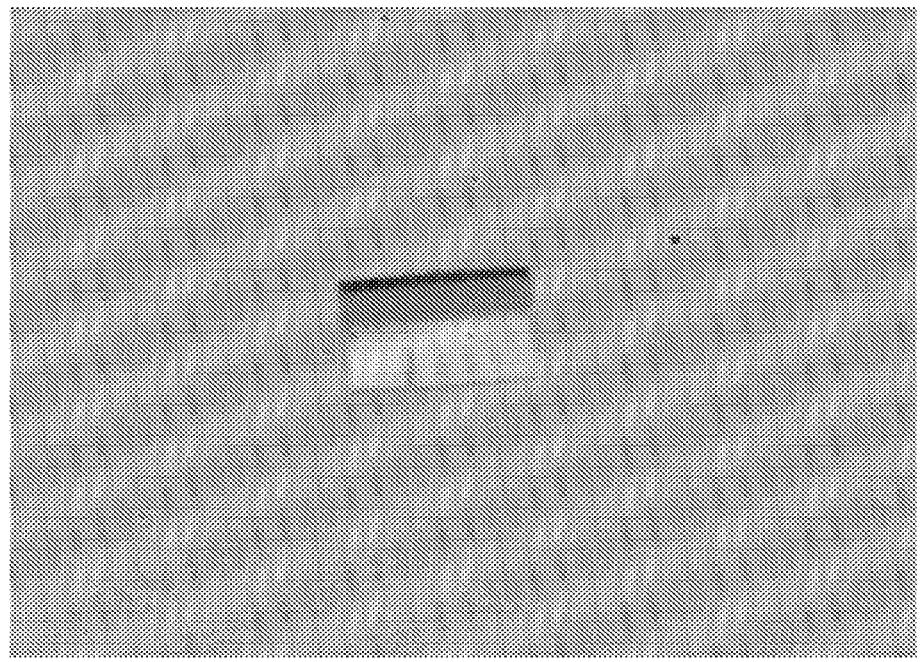
FIG. 6 is a micrograph of a polymer-metal complex crystal including cyclohexane

FIG. 6 shows a micrograph of the single crystal.

Note that the occupancy ratio of cyclohexane was 100%.

TABLE 1

| Crystal system | Monoclinic |
| --- | --- |
| Space group | C2/c |
| a (Å) | 34.559 |
| b (Å) | 15.111 |
| c (Å) | 30.058 |
| α (°) | 90 |
| β (°) | 100.510 |
| γ (°) | 90 |
| Z | 8 |
| R1 | 11.48 |

Elemental Analysis Results
　Found: C: 37.67%, H: 3.53%, N: 8.75%.
　Cald.: C: 37.56%, H: 3.78%, N: 8.76%.

Figure 7:
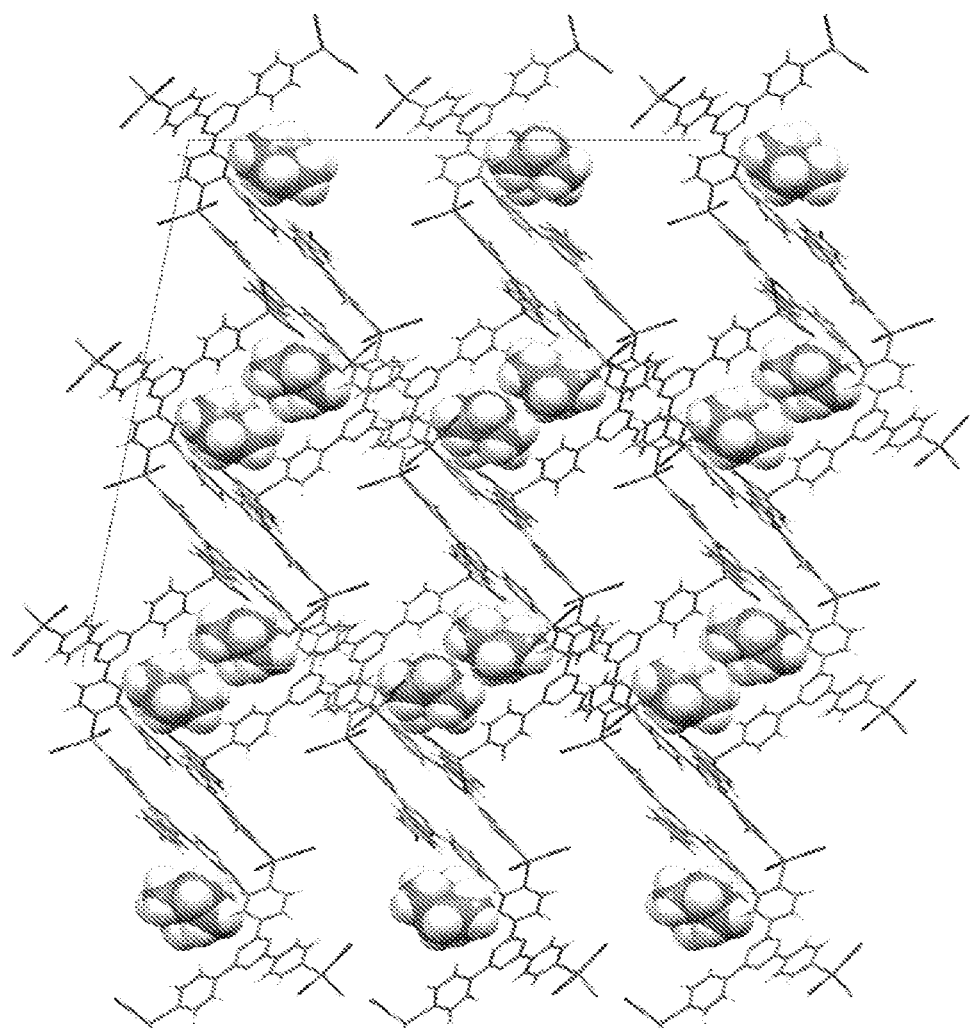
FIG. 7 is a view illustrating the polymer-metal complex crystal including cyclohexane obtained in Example 1.
Figure 8:
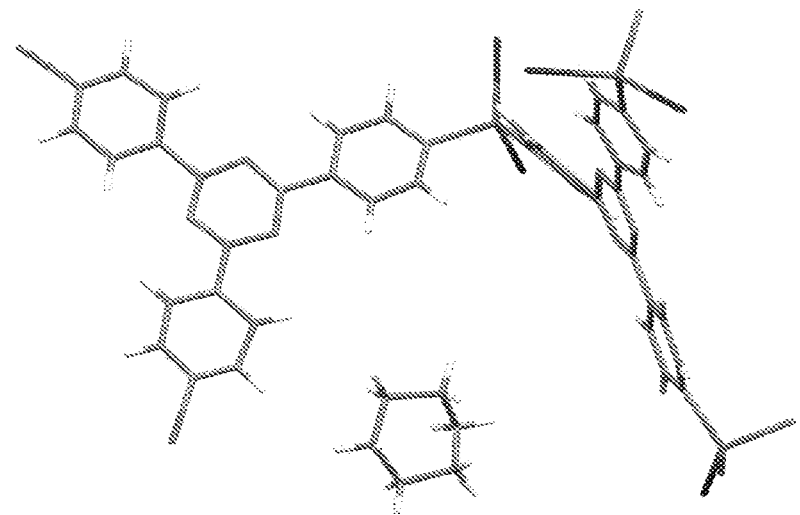
FIG. 8 is an enlarged view illustrating the polymer-metal complex crystal including cyclohexane obtained in Example 1.

FIGS. 7 and 8 show the crystal structure of the resulting polymer-metal complex crystal including cyclohexane.

Example 2: Synthesis of Polymer-Metal Complex Crystal Including Ethyl Acetate 10 mg of the single crystal of the polymer-metal complex 1 obtained in the step 1 of Example 1 was immersed in 10 mL of ethyl acetate for 7 days under the same conditions as those employed in the step 2 of Example 1 to saturate the pores and the like of the single crystal with ethyl acetate. The resulting complex crystal was filtered off, and subjected to elemental analysis. It was thus found that the complex crystal was a polymer-metal complex $[(ZnI_2)_3(TPT)_2(AcOEt)_3]$ in which ethyl acetate (AcOEt) was included in the pores and the like.

Elemental Analysis Results
　Found: C: 31.36%, H: 2.38%, N: 9.30%.
　Cald.: C: 31.22%, H: 2.62%, N: 9.10%.

Example 3: Synthesis of Polymer-Metal Complex Crystal Including Heptane 10 mg of the single crystal of the polymer-metal complex 1 obtained in the step 1 of Example 1 was immersed in 10 mL of heptane for 7 days under the same conditions as those employed in the step 2 of Example 1 to saturate the pores and the like of the single crystal with heptane. The resulting complex crystal was filtered off, and subjected to elemental analysis. It was thus found that the complex crystal was a polymer-metal complex $[(ZnI_2)_3(TPT)_2(PhNO_2)(heptane)_{2.5}]$ in which heptane was included in the pores and the like.

Elemental Analysis Results
　Found: C: 36.68%, H: 3.60%, N: 9.43%.
　Cald.: C: 36.54%, H: 3.56%, N: 9.31%.

Example 4: Synthesis of Polymer-Metal Complex Crystal Including Toluene 10 mg of the single crystal of the polymer-metal complex 1 obtained in the step 1 of Example 1 was immersed in 10 mL of toluene for 7 days under the same conditions as those employed in the step 2 of Example 1 to saturate the pores and the like of the single crystal with toluene. The resulting complex crystal was filtered off, and subjected to elemental analysis. It was thus found that the complex crystal was a polymer-metal complex $[(ZnI_2)_3(TPT)_2(toluene)_5]$ in which toluene was included in the pores and the like.

Elemental Analysis Results
　Found: C: 42.12%, H: 3.04%, N: 8.26%.
　Cald.: C: 41.74%, H: 3.16%, N: 8.23%.

Example 5: Synthesis of Polymer-Metal Complex Crystal Including 1,2-Dimethoxyethane 10 mg of the single crystal of the polymer-metal complex 1 obtained in the step 1 of Example 1 was immersed in 10 mL of 1,2-dimethoxyethane (DME) for 7 days under the same conditions as those employed in the step 2 of Example 1 to saturate the pores and the like of the single crystal with DME. The resulting complex crystal was filtered off, and subjected to elemental analysis. It was thus found that the complex crystal was a polymer-metal complex $[(ZnI_2)_3(TPT)_2(DME)_{2.5}]$ in which DME was included in the pores and the like.

Elemental Analysis Results
　Found: C: 30.87%, H: 2.53%, N: 9.07%.
　Cald.: C: 30.57%, H: 2.73%, N: 9.30%.

Example 6: Synthesis of Polymer-Metal Complex Crystal Including Acetonitrile 10 mg of the single crystal of the polymer-metal complex 1 obtained in the step 1 of Example 1 was immersed in 10 mL of acetonitrile ($CH_3CN$) for 7 days under the same conditions as those employed in the step 2 of Example 1 to saturate the pores and the like of the single crystal with $CH_3CN$. The resulting complex crystal was filtered off, and subjected to elemental analysis. It was thus found that the complex crystal was a polymer-metal complex $[(ZnI_2)_3(TPT)_2(CH_3CN)_{3.25}]$ in which $CH_3CN$ was included in the pores and the like.

Elemental Analysis Results
　Found: C: 29.92%, H: 1.68%, N: 12.19%.
　Cald.: C: 29.75%, H: 1.98%, N: 12.45%.

Example 7: Synthesis of Polymer-Metal Complex Crystal Including Carbon Tetrachloride 10 mg of the single crystal of the polymer-metal complex 1 obtained in the step 1 of Example 1 was immersed in 10 mL of carbon tetrachloride ($CCl_4$) for 7 days under the same conditions as those employed in the step 2 of Example 1 to saturate the pores and the like of the single crystal with carbon tetrachloride. The resulting complex crystal was filtered off, and subjected to elemental analysis. It was thus found that the complex crystal was a polymer-metal complex [(ZnI$_2$)$_3$(TPT)$_2$(CCl$_4$)$_5$] in which carbon tetrachloride was included in the pores and the like.
Elemental Analysis Results
Found: C: 20.77%, H: 0.75%, N: 6.93%.
Cald.: C: 20.94%, H: 1.03%, N: 7.15%.

Example 8: Synthesis of Polymer-Metal Complex Including Cyclohexane 6.3 mg of TPT was dissolved in a nitrobenzene/methanol (4 mL/1 mL) mixture to obtain a ligand solution.

Separately, 9.6 mg of ZnI$_2$ was dissolved in 1 mL of methanol to obtain a metal ion-containing solution.

The ligand solution was put in a test tube (diameter: 15 mm, height: 12 cm), and the metal ion-containing solution was slowly added to the test tube so as to form a layer on the ligand solution. The solutions were allowed to stand at 15 to 25° C. for 7 days to obtain a polymer-metal complex crystal.

The resulting crystal was identified by elemental analysis, thermogravimetry-mass spectrometry, and X-ray single crystal structure analysis in the same manner as in Example 1, and found to be [(ZnI$_2$)$_3$(TPT)$_2$(PhNO$_2$)$_{5.5}$]$_n$.

100 mg of the single crystal of the polymer-metal complex including nitrobenzene obtained as described above was immersed in 10 mL of cyclohexane for 2 days under the same conditions as those employed in Example 1 to saturate the pores of the single crystal with cyclohexane. The single crystal was then removed, and subjected to elemental analysis and crystal structure analysis. It was found that the single crystal was a compound having the composition [(ZnI$_2$)$_3$(TPT)$_2$(cyclohexane)$_4$]$_n$.

Example 9: Synthesis of Polymer-Metal Complex Crystal Including Dichlorobenzene 6.3 mg of TPT was dissolved in 5 mL of a 1,2-dichlorobenzene/methanol (volume ratio: 4:1) mixture in a test tube. A solution prepared by dissolving 7.0 mg of cobalt(II) thiocyanate in 1 mL of methanol was slowly added to the above solution, and the solutions separated in two layers were allowed to stand at room temperature for 2 days.

An orange crystal that precipitated on the wall of the test tube was filtered off to obtain 9.9 mg of a polymer-metal complex (yield: 52%).

The resulting polymer-metal complex was subjected to elemental analysis and X-ray single crystal structural analysis, and found to be (TPT)$_4${Co(SCN)$_2$}$_3$(Cl$_2$C$_6$H$_4$)$_{2.5}$(MeOH)$_5$ having the same structure as that illustrated in FIG. 4. The polymer-metal complex included twenty-five 1,2-dichlorobenzene molecules and five methanol molecules per regular octahedral structural unit.
Elemental Analysis Results
Found: C: 49.60%, H: 2.92%, N: 7.43%.
Cald.: C: 49.89%, H: 3.02%, N: 7.48%.
X-Ray Single Crystal Structural Analysis Results
Lattice constant: a=b=c=37.599 Å, cubic, space group: Fm-3m Example 10: Synthesis of Polymer-Metal Complex Crystal Including 2-methyl-1,4-naphthoquinone A micro vial with a septum cap was charged with 50 µL of ethyl acetate, and one piece (size: 150×150×100 µm, theoretical amount of a substance having a specific gravity of 1 required to fill the pores therewith: 1.13 µg) of the single crystal of the polymer-metal complex including ethyl acetate ([(ZnI$_2$)$_3$(TPT)$_2$(AcOEt)$_3$]) obtained in Example 2 was immersed in ethyl acetate contained in the micro vial.

2-Methyl-1,4-naphthoquinone was dissolved in dichloromethane at a concentration of 1 µg/1 µL, and 5 µL of the resulting sample solution (including 2-methyl-1,4-naphthoquinone in an amount of 5 µg) was added to the micro vial. The value A in Example 10 was 4.4.

After fastening the cap on the micro vial, a pinhole was formed in the septum using a syringe needle (hole diameter: 0.8 mm), and the micro vial was allowed to stand in a temperature-controlled room at 45° C. for 2 days.

The organic solvent (ethyl acetate and dichloromethane) contained in the micro vial volatilized at a volatilization rate of about 48 µL/24 hours under the above conditions, and the solution was concentrated.

The single crystal was then removed, mounted on an X-ray crystal structure analyzer, and subjected to crystal structure analysis.

Figure 9:
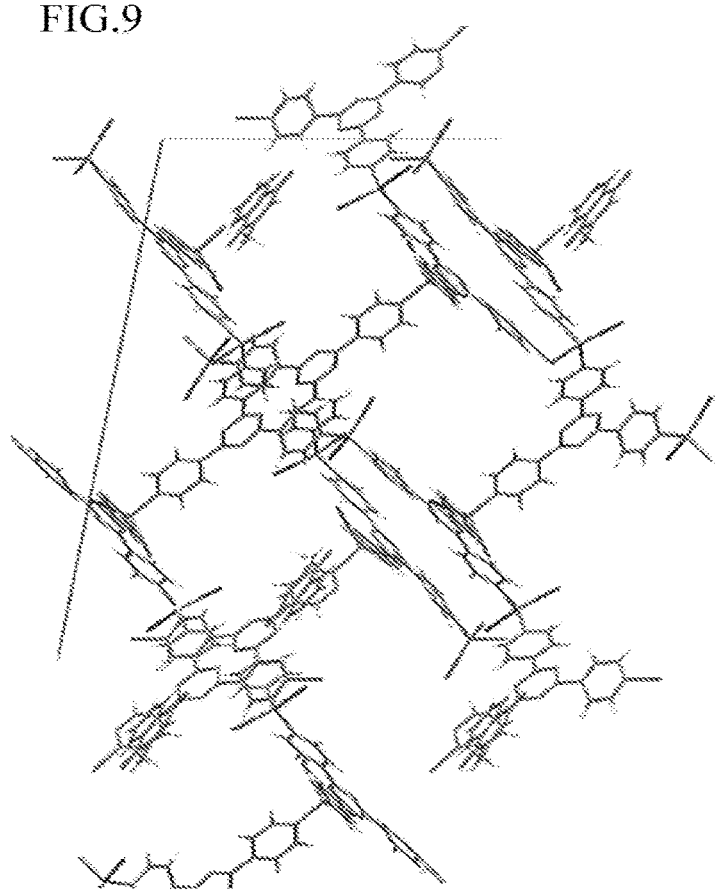
FIG. 9 is a view illustrating the polymer-metal complex including 2-methyl-1,4-naphthoquinone obtained in Example 9.
Figure 10:
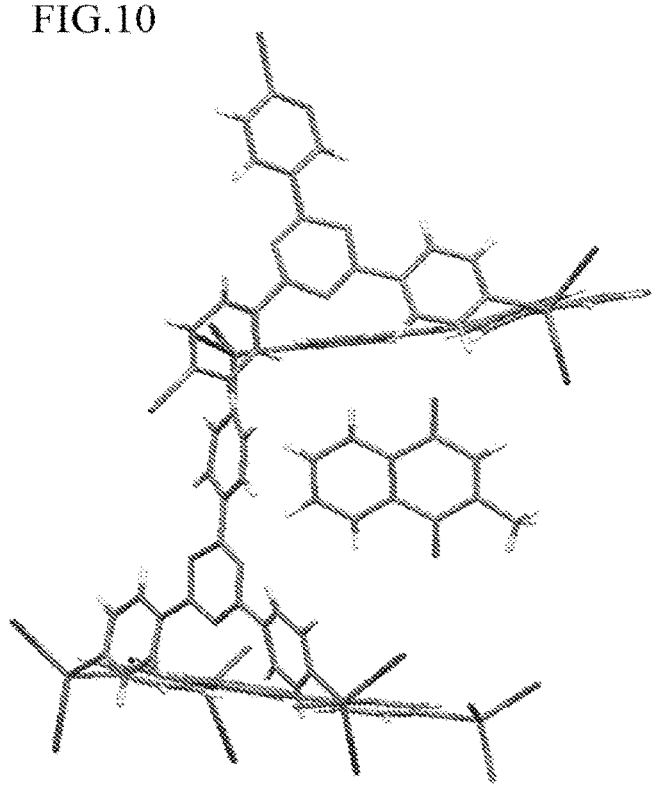
FIG. 10 is an enlarged view illustrating the polymer-metal complex including 2-methyl-1,4-naphthoquinone obtained in Example 9.

Tables 2 shows the crystallographic data, and FIGS. 9 and 10 show the crystal structure.

TABLE 2

| Crystal system | Triclinic |
|---|---|
| Space group | P-1 |
| a (Å) | 14.991 |
| b (Å) | 18.774 |
| c (Å) | 30.118 |
| α (°) | 98.981 |
| β (°) | 92.187 |
| γ (°) | 110.596 |
| Z | 2 |
| R1 | 13.31 |

Example 11: Synthesis of Polymer-Metal Complex Crystal Including 4-cyano-4'-pentylbiphenyl A micro vial with a septum cap was charged with 50 µL of heptane, and one piece (size: 200×60×50 µm, theoretical amount of a substance having a specific gravity of 1 required to fill the pores therewith: 0.30 µg) of the single crystal of the polymer-metal complex including heptane ([(ZnI$_2$)$_3$(TPT)$_2$(nitrobenzene)(heptane)$_{2.5}$]) obtained in Example 2 was immersed in heptane contained in the micro vial.

4-Cyano-4'-pentylbiphenyl was dissolved in dichloromethane at a concentration of 1 µg/1 µL, and 5 µL of the resulting sample solution (including 4-cyano-4'-pentylbiphenyl in an amount of 5 µg) was added to the micro vial. The value A in Example 11 was 16.6.

After fastening the cap on the micro vial, a pinhole was formed in the septum using a syringe needle (hole diameter: 0.8 mm), and the micro vial was allowed to stand in a temperature-controlled room at 45° C. for 2 days.

The organic solvent (heptane and dichloromethane) contained in the micro vial volatilized at a volatilization rate of about 48 µL/24 hours under the above conditions, and the solution was concentrated.

The single crystal was then removed, mounted on an X-ray crystal structure analyzer, and subjected to crystal structure analysis.

Figure 11:
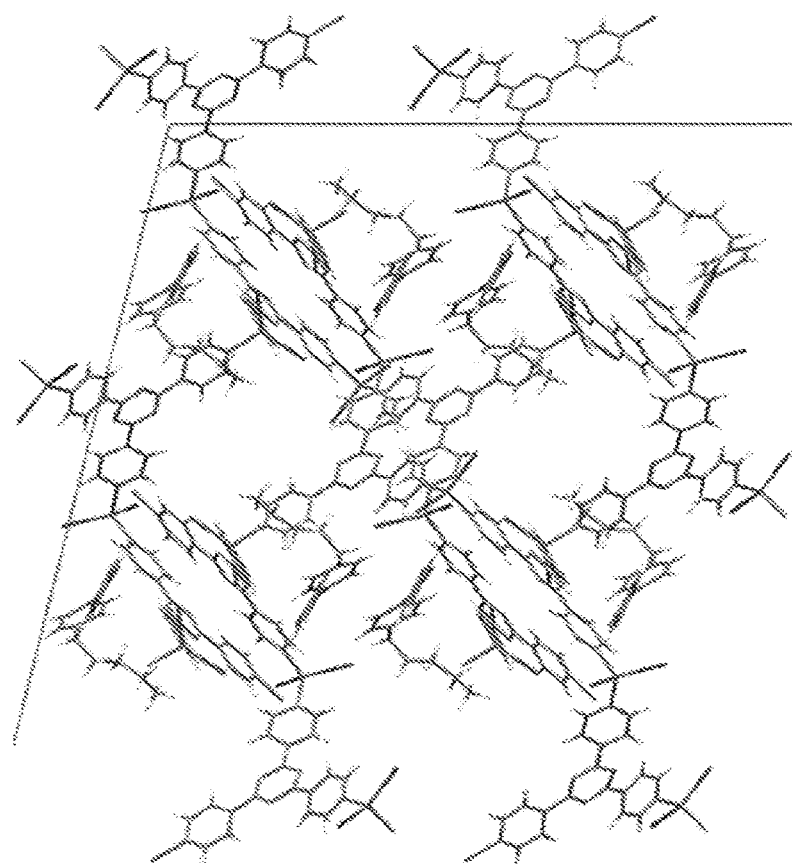
FIG. 11 is a view illustrating the polymer-metal complex including 4-cyano-4'-pentylbiphenyl obtained in Example 10.
Figure 12:
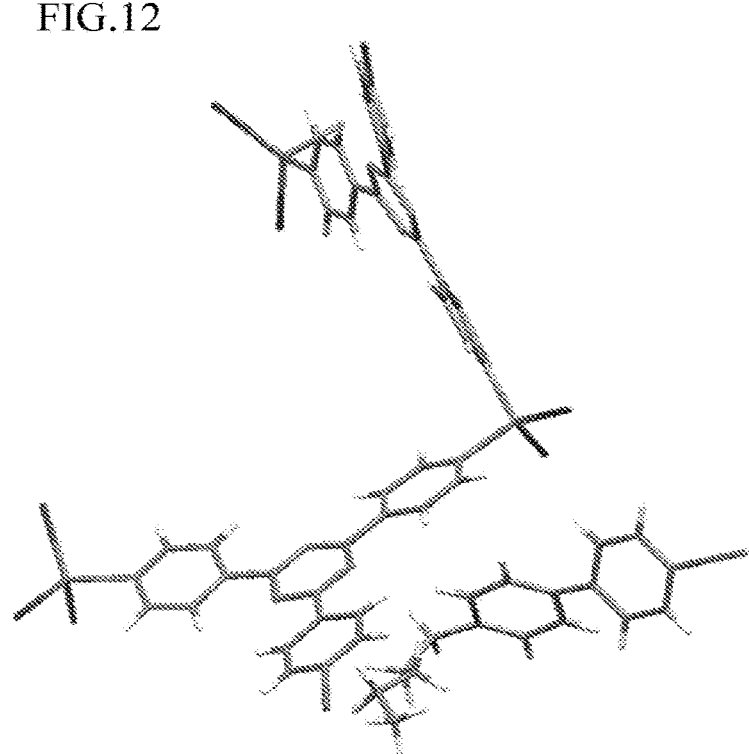
FIG. 12 is an enlarged view illustrating the polymer-metal complex including 4-cyano-4'-pentylbiphenyl obtained in Example 10.

Tables 3 shows the crystallographic data, and FIGS. 11 and 12 show the crystal structure.

TABLE 3

| | |
|---|---|
| Crystal system | Monoclinic |
| Space group | C2/c |
| a (Å) | 35.562 |
| b (Å) | 14.7759 |
| c (Å) | 31.573 |
| α (°) | 90 |
| β (°) | 102.981 |
| γ (°) | 90 |
| Z | 8 |
| R1 | 7.54 |

Example 12: Synthesis of Polymer-Metal Complex Crystal Including 1,4-dimethyl-7-isopropylazulene A micro vial with a septum cap (see (a) in FIG. 5) was charged with 50 µL of cyclohexane, and one piece (size: 100×100×60 µm, theoretical amount of a substance having a specific gravity of 1 required to fill the pores therewith: 0.3 µg) of the single crystal of the polymer-metal complex including cyclohexane obtained in Example 8 was immersed in cyclohexane contained in the micro vial.

1,4-Dimethyl-7-isopropylazulene was dissolved in dichloromethane at a concentration of 1 µg/1 µL, and 5 µL of the resulting sample solution (including 1,4-dimethyl-7-isopropylazulene in an amount of 5 µg) was added to the micro vial. The value A in Example 12 was 16.7.

After fastening the cap on the micro vial, a pinhole was formed in the septum using a syringe needle (hole diameter: 0.8 mm), and the micro vial was allowed to stand in a temperature-controlled room at 45° C. for 2 days.

The organic solvent (cyclohexane and dichloromethane) contained in the micro vial volatilized at a volatilization rate of about 48 µL/24 hours under the above conditions, and the solution was concentrated.

The single crystal was then removed, mounted on an X-ray crystal structure analyzer, and subjected to crystal structure analysis.

Figure 13:
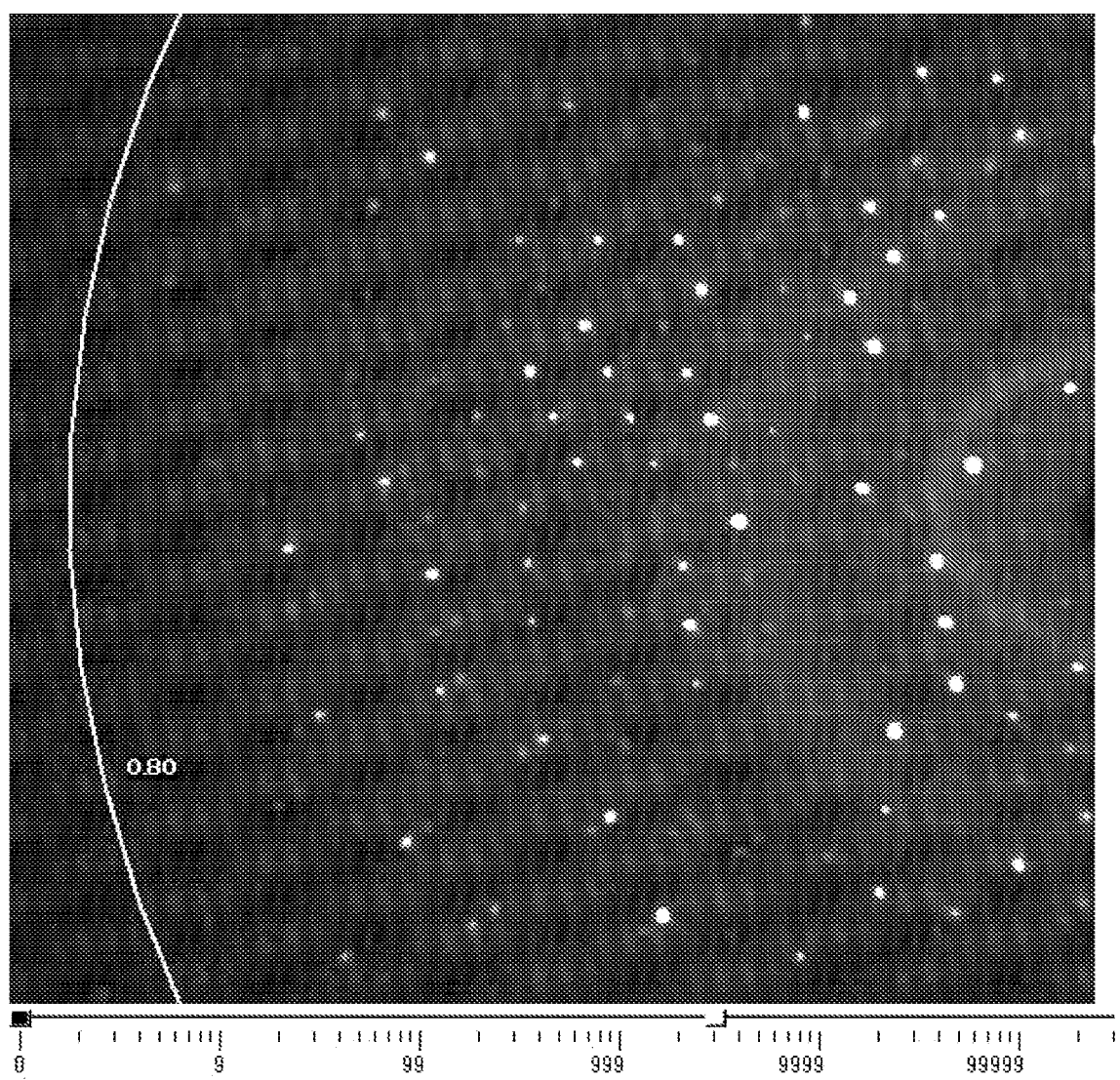
FIG. 13 is a view illustrating a diffraction pattern (Example 11).

The diffraction pattern illustrated in FIG. 13 was obtained at an exposure time of 30 seconds, and the resolution was 0.8 Å or more.

Figure 14:
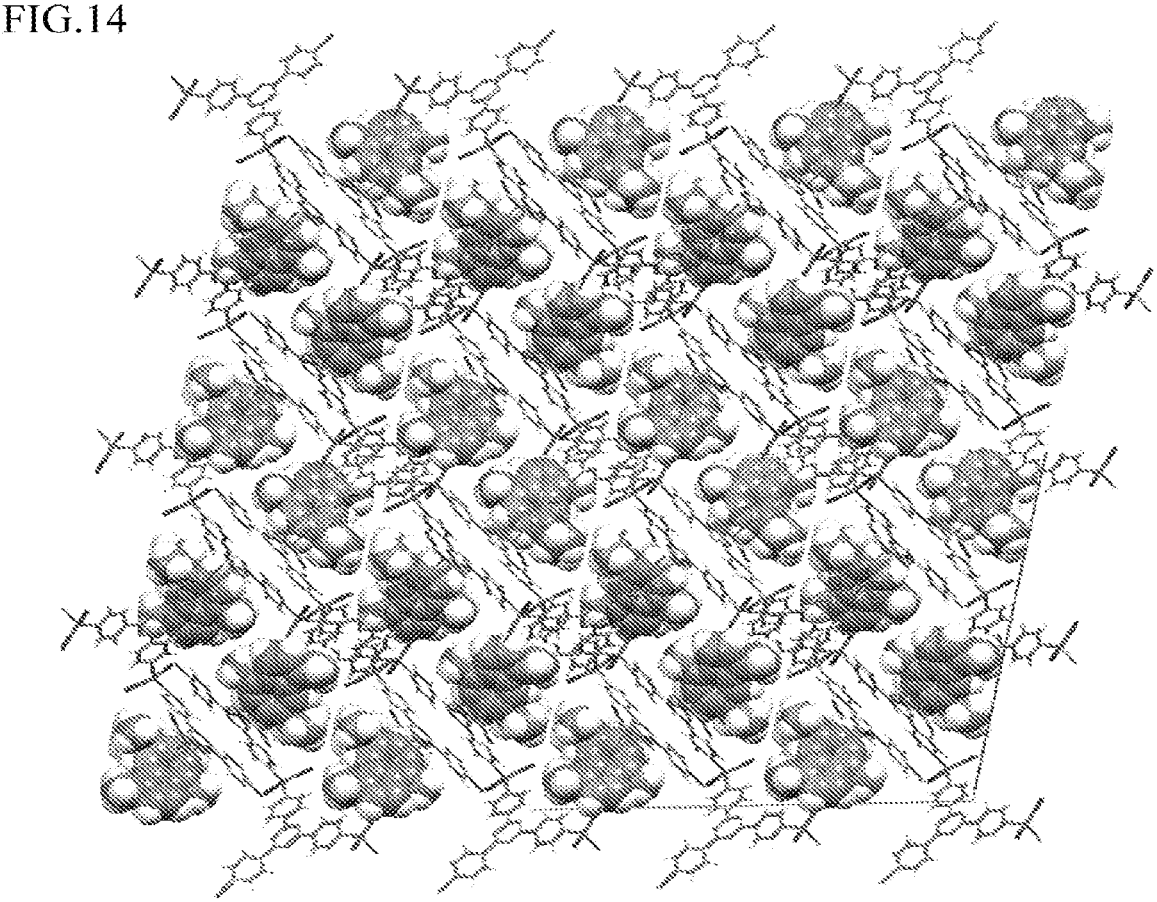
FIG. 14 is a view illustrating the polymer-metal complex including 1,4-dimethyl-7-isopropylazulene obtained in Example 11.
Figure 15:
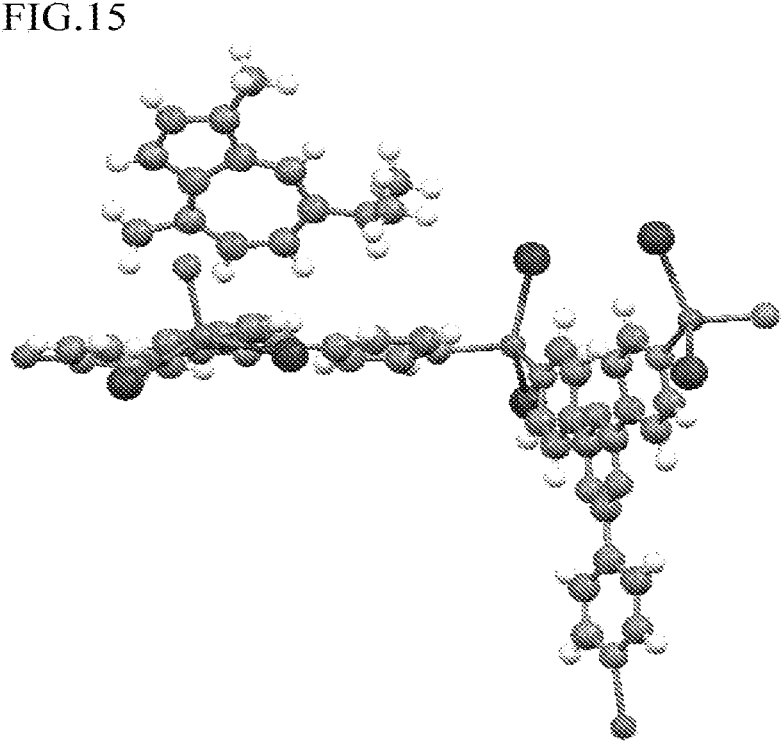
FIG. 15 is an enlarged view illustrating the polymer-metal complex including 1,4-dimethyl-7-isopropylazulene obtained in Example 11.

Tables 4 shows the crystallographic data, and FIGS. 14 and 15 show the crystal structure. Note that the occupancy ratio of 1,4-dimethyl-7-isopropylazulene was 73%.

TABLE 4

| | |
|---|---|
| Crystal system | Monoclinic |
| Space group | C2/c |
| a (Å) | 34.942 |
| b (Å) | 14.8462 |
| c (Å) | 30.976 |
| α (°) | 90 |
| β (°) | 102.149 |
| γ (°) | 90 |
| Z | 8 |
| R1 | 10.6 |

Example 13: Synthesis of Polymer-Metal Complex Crystal Including (3S,3aS,5aS,9bS)-3a,5,5a,9b-tetrahydro-3,5a,9-trimethylnaphtho[1,2-b]furan-2,8(3H,4H)-dione A micro vial with a septum cap (see (a) in FIG. 5) was charged with 50 µL of cyclohexane, and one piece (size: 350×70×50 µm, theoretical amount of a substance having a specific gravity of 1 required to fill the pores therewith: 0.61 µg) of the single crystal obtained in Example 8 was immersed in cyclohexane contained in the micro vial.

(3S,3aS,5aS,9bS)-3a,5,5a,9b-Tetrahydro-3,5a,9-trimethylnaphtho[1,2-b]furan-2,8(3H,4H)-dione was dissolved in dichloromethane at a concentration of 1 µg/1 µL, and 5 µL of the resulting sample solution (including (3S,3aS,5aS,9bS)-3a,5,5a,9b-tetrahydro-3,5a,9-trimethylnaphtho[1,2-b]furan-2,8(3H,4H)-dione in an amount of 5 µg) was added to the micro vial. The value A in Example 13 was 8.2.

After fastening the cap on the micro vial, a pinhole was formed in the septum using a syringe needle (hole diameter: 0.8 mm), and the micro vial was allowed to stand in a temperature-controlled room at 45° C. for 2 days.

The organic solvent (cyclohexane and dichloromethane) contained in the micro vial volatilized at a volatilization rate of about 48 µL/24 hours under the above conditions, and the solution was concentrated.

The single crystal was then removed, mounted on an X-ray crystal structure analyzer, and subjected to crystal structure analysis.

Figure 16:
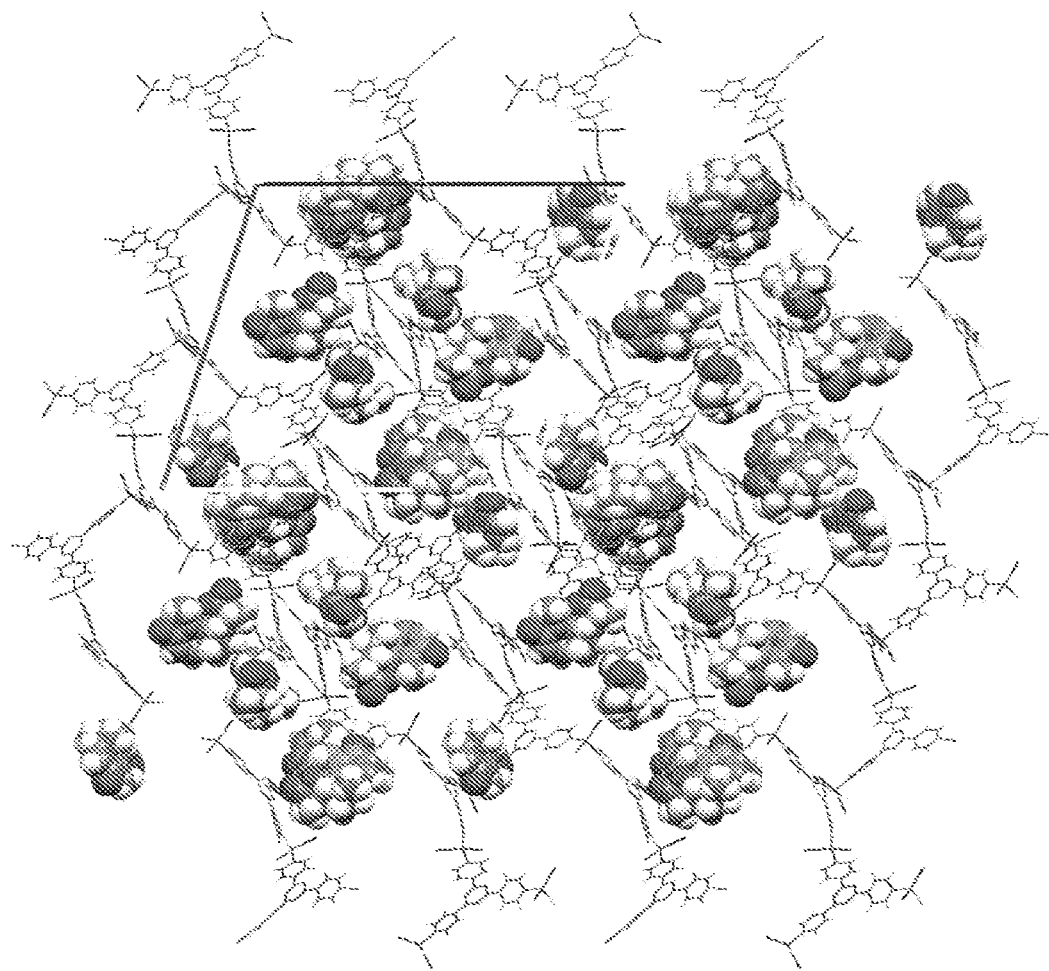
FIG. 16 is a view illustrating the polymer-metal complex including (3S,3aS,5aS,9bS)-3a,5,5a,9b-tetrahydro-3,5a,9-trimethylnaphtho[1,2-b]furan-2,8(3H,4H)-dione obtained in Example 12.
Figure 17:
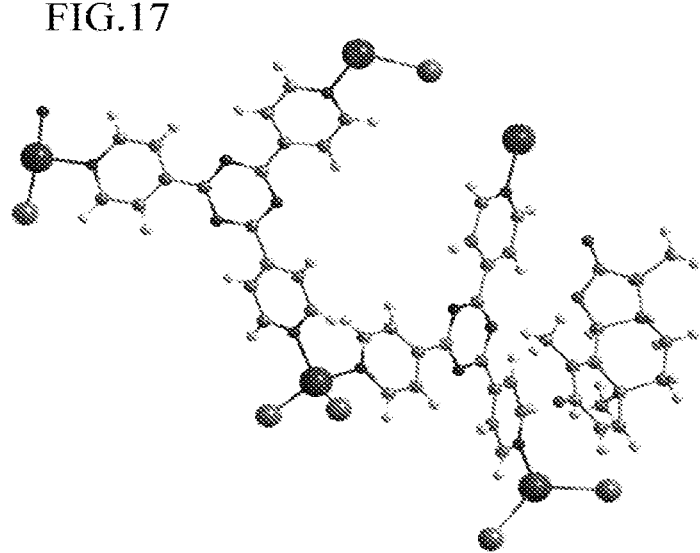
FIG. 17 is an enlarged view illustrating the polymer-metal complex including (3S,3aS,5aS,9bS)-3a,5,5a,9b-tetrahydro-3,5a,9-trimethylnaphtho[1,2-b]furan-2,8(3H,4H)-dione obtained in Example 12.

Tables 5 shows the crystallographic data, and FIGS. 16 and 17 show the crystal structure. Note that the occupancy ratio of (3S,3aS,5aS,9bS)-3a,5,5a,9b-tetrahydro-3,5a,9-trimethylnaphtho[1,2-b]furan-2,8(3H,4H)-dione was 100%.

TABLE 5

| | |
|---|---|
| Crystal system | Monoclinic |
| Space group | P2$_1$ |
| a (Å) | 32.866 |
| b (Å) | 14.853 |
| c (Å) | 34.85 |
| α (°) | 90 |
| β (°) | 105.848 |
| γ (°) | 90 |
| Z | 2 |
| R1 | 8.27 |

Example 14: Synthesis of Polymer-Metal Complex Crystal Including 2-(3,4-dimethoxyphenyl)-5,6,7,8-tetramethoxy-4H-1-benzopyran-4-one A micro vial with a septum cap (see (a) in FIG. 5) was charged with 50 µL of cyclohexane, and one piece (size: 130×110×80 µm, theoretical amount of a substance having a specific gravity of 1 required to fill the pores therewith: 0.57 µg) of the single crystal obtained in Example 8 was immersed in cyclohexane contained in the micro vial.

2-(3,4-Dimethoxyphenyl)-5,6,7,8-tetramethoxy-4H-1-benzopyran-4-one was dissolved in dichloromethane at a concentration of 1 µg/1 µL, and 5 µL of the resulting sample solution (including 2-(3,4-dimethoxyphenyl)-5,6,7,8-tetramethoxy-4H-1-benzopyran-4-one in an amount of 5 µg) was added to the micro vial. The value A in Example 14 was 8.8.

After fastening the cap on the micro vial, a pinhole was formed in the septum using a syringe needle (hole diameter: 0.8 mm), and the micro vial was allowed to stand in a temperature-controlled room at 45° C. for 2 days.

The organic solvent (cyclohexane and dichloromethane) contained in the micro vial volatilized at a volatilization rate of about 48 µL/24 hours under the above conditions, and the solution was concentrated.

The single crystal was then removed, mounted on an X-ray crystal structure analyzer, and subjected to crystal structure analysis.

Figure 18:
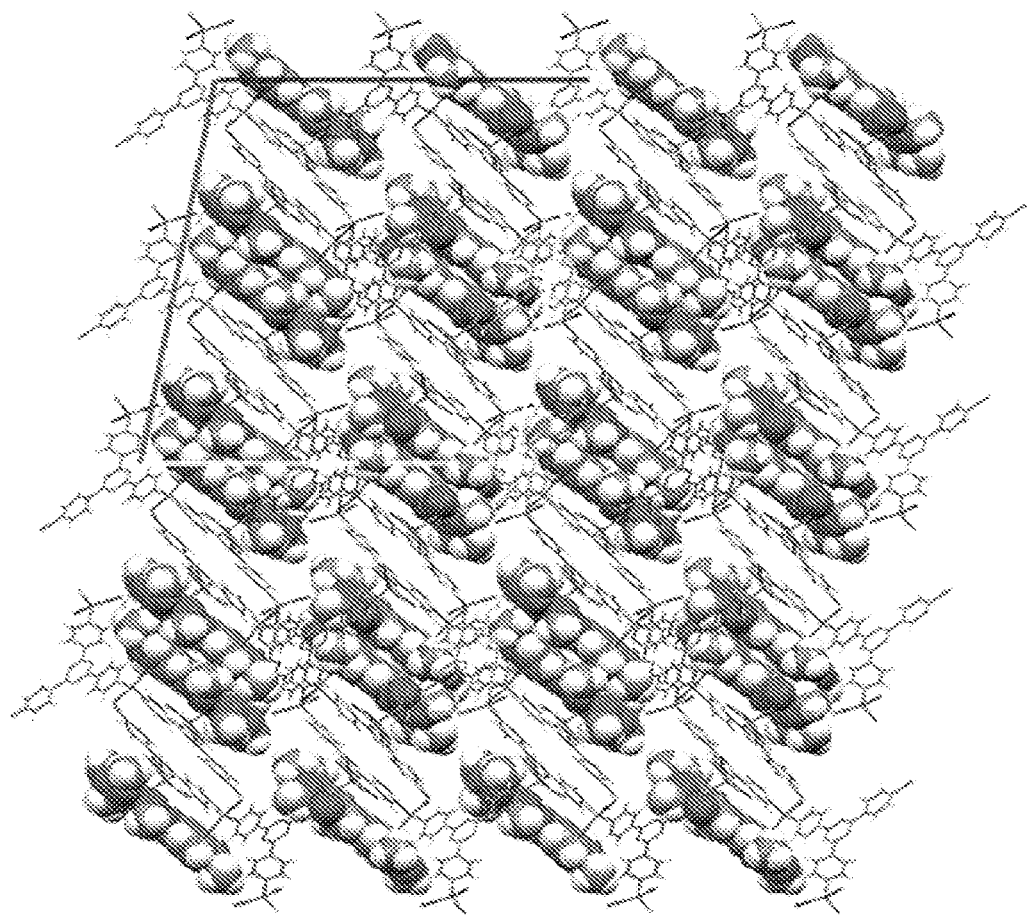
FIG. 18 is a view illustrating the polymer-metal complex including 2-(3,4-dimethoxyphenyl)-5,6,7,8-tetramethoxy-4H-1-benzopyran-4-one obtained in Example 13.
Figure 19:
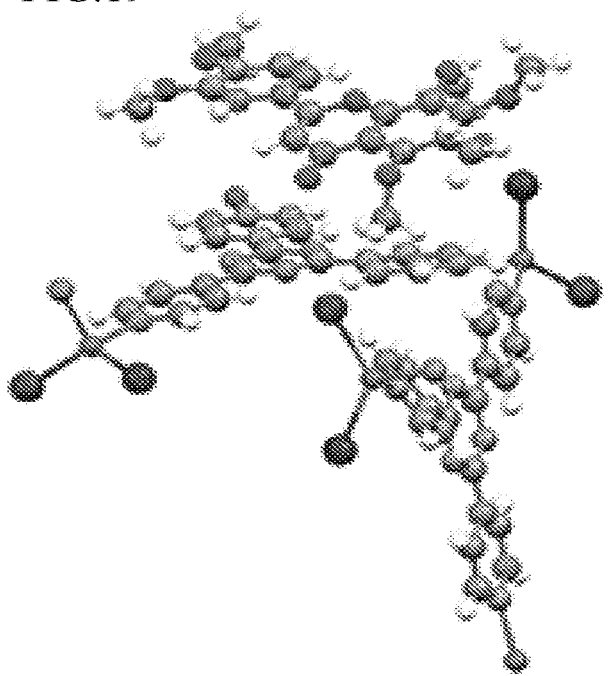
FIG. 19 is an enlarged view illustrating the polymer-metal complex including 2-(3,4-dimethoxyphenyl)-5,6,7,8-tetramethoxy-4H-1-benzopyran-4-one obtained in Example 13.

Tables 6 shows the crystallographic data, and FIGS. 18 and 19 show the crystal structure. Note that the occupancy ratio of 2-(3,4-dimethoxyphenyl)-5,6,7,8-tetramethoxy-4H-1-benzopyran-4-one was 53%.

TABLE 6

| Crystal system | Monoclinic |
| --- | --- |
| Space group | C2/c |
| a (Å) | 34.562 |
| b (Å) | 14.95 |
| c (Å) | 30.348 |
| α (°) | 90 |
| β (°) | 100.119 |
| γ (°) | 90 |
| Z | 8 |
| R1 | 13.13 |

Example 15: Synthesis of Polymer-Metal Complex Crystal Including 5,6,7,8-tetramethoxy-2-(4-methoxyphenyl)-4H-1-benzopyran-4-one A micro vial with a septum cap (see (a) in FIG. 5) was charged with 50 μL of cyclohexane, and one piece (size: 300×100×100 μm, theoretical amount of a substance having a specific gravity of 1 required to fill the pores therewith: 1.5 μg) of the single crystal obtained in Example 8 was immersed in cyclohexane contained in the micro vial.

5,6,7,8-Tetramethoxy-2-(4-methoxyphenyl)-4H-1-benzopyran-4-one was dissolved in dichloromethane at a concentration of 2 μg/1 μL, and 2.5 μL of the resulting sample solution (including 5,6,7,8-tetramethoxy-2-(4-methoxyphenyl)-4H-1-benzopyran-4-one in an amount of 5 μg) was added to the micro vial. The value A in Example 15 was 3.3.

After fastening the cap on the micro vial, a pinhole was formed in the septum using a syringe needle (hole diameter: 0.8 mm), and the micro vial was allowed to stand in a temperature-controlled room at 45° C. for 2 days.

The organic solvent (cyclohexane and dichloromethane) contained in the micro vial volatilized at a volatilization rate of about 48 μL/24 hours under the above conditions, and the solution was concentrated.

The single crystal was then removed, mounted on an X-ray crystal structure analyzer, and subjected to crystal structure analysis.

Figure 20:
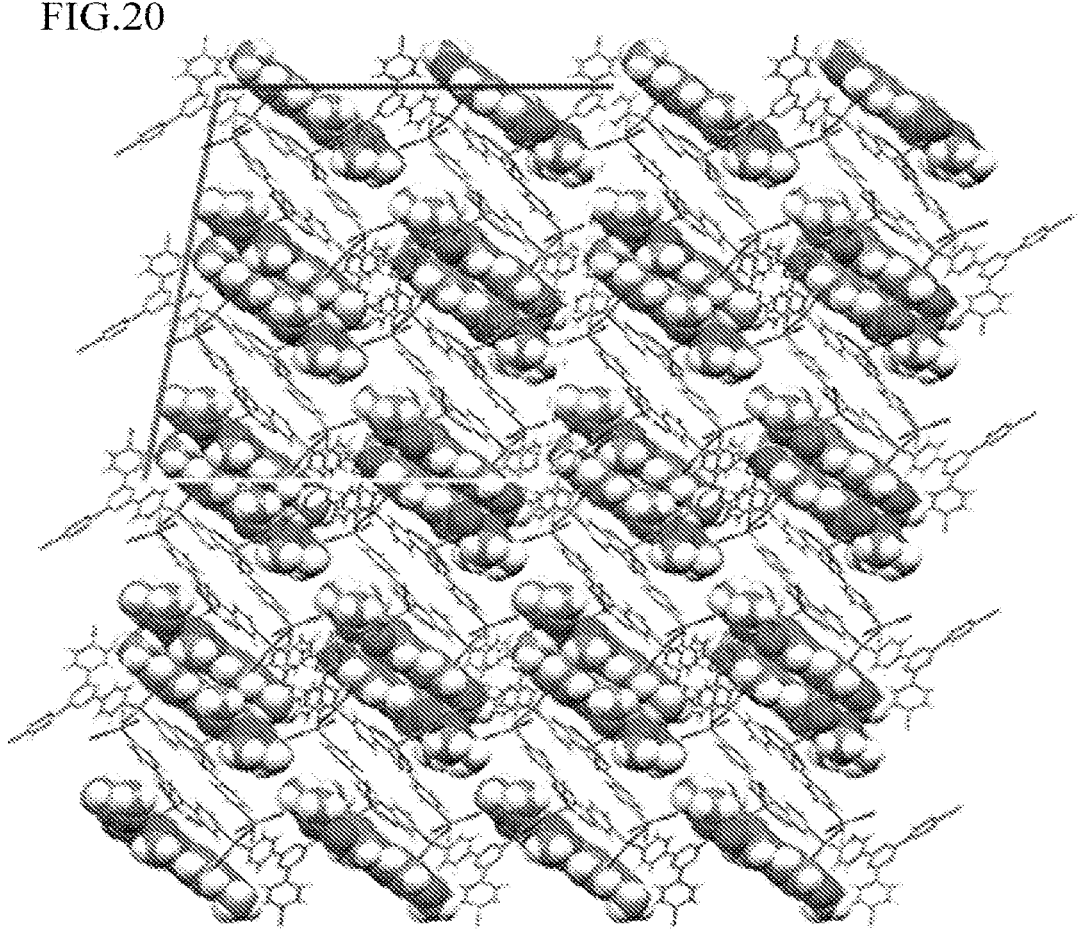
FIG. 20 is a view illustrating the polymer-metal complex including 5,6,7,8-tetramethoxy-2-(4-methoxyphenyl)-4H-1-benzopyran-4-one obtained in Example 14.
Figure 21:
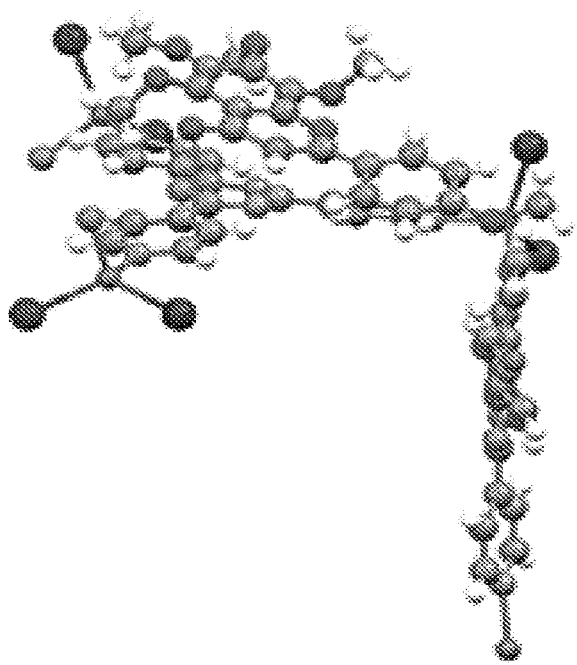
FIG. 21 is an enlarged view illustrating the polymer-metal complex including 5,6,7,8-tetramethoxy-2-(4-methoxyphenyl)-4H-1-benzopyran-4-one obtained in Example 14.

Tables 7 shows the crystallographic data, and FIGS. 20 and 21 show the crystal structure. Note that the occupancy ratio of 5,6,7,8-tetramethoxy-2-(4-methoxyphenyl)-4H-1-benzopyran-4-one was 80%.

TABLE 7

| Crystal system | Monoclinic |
| --- | --- |
| Space group | C2/c |
| a (Å) | 34.103 |
| b (Å) | 14.767 |
| c (Å) | 30.7 |
| α (°) | 90 |
| β (°) | 99.802 |
| γ (°) | 90 |
| Z | 8 |
| R1 | 9.52 |

Example 16

100 mg of the single crystal of the cobalt complex obtained in Example 9 was immersed in 10 mL of toluene for 2 days to saturate the pores of the single crystal with toluene.

A micro vial with a septum cap (see (a) in FIG. 5) was charged with 50 μL of toluene, and one piece (size: 320×300×280 μm, theoretical amount of a substance having a specific gravity of 1 required to fill the pores therewith: 21.0 μg) of the single crystal that had been immersed in toluene, was immersed in toluene contained in the micro vial. The value A in Example 16 was 0.31.

2,2'-Bithiophene was dissolved in toluene at a concentration of 1 μg/1 μL, and 5 μL of the resulting sample solution (including 2,2'-bithiophene in an amount of 5 μg was added to the micro vial.

After allowing the mixture to stand at 45° C. for 2 days, the single crystal was removed, mounted on an X-ray crystal structure analyzer, and subjected to crystal structure analysis.

Figure 22:
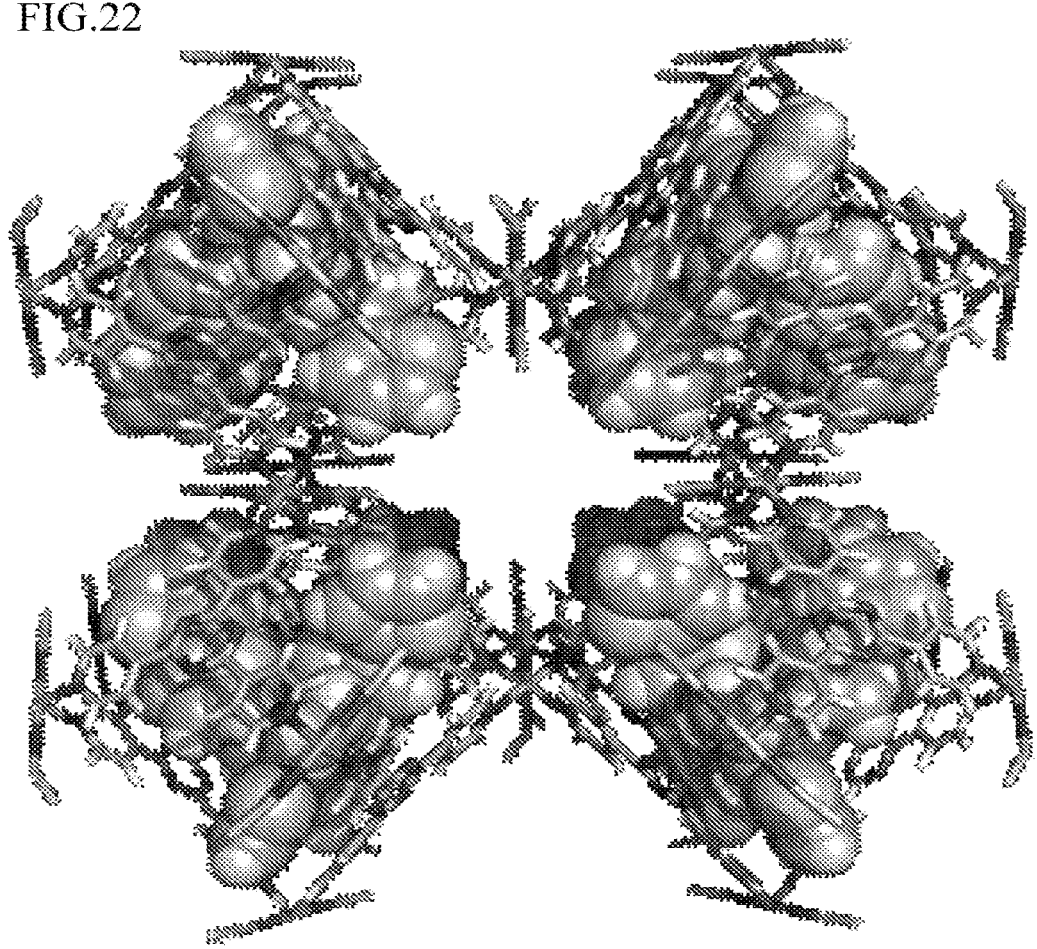
FIG. 22 is a view illustrating the polymer-metal complex including 2,2'-bithiophene obtained in Example 16.
Figure 23:
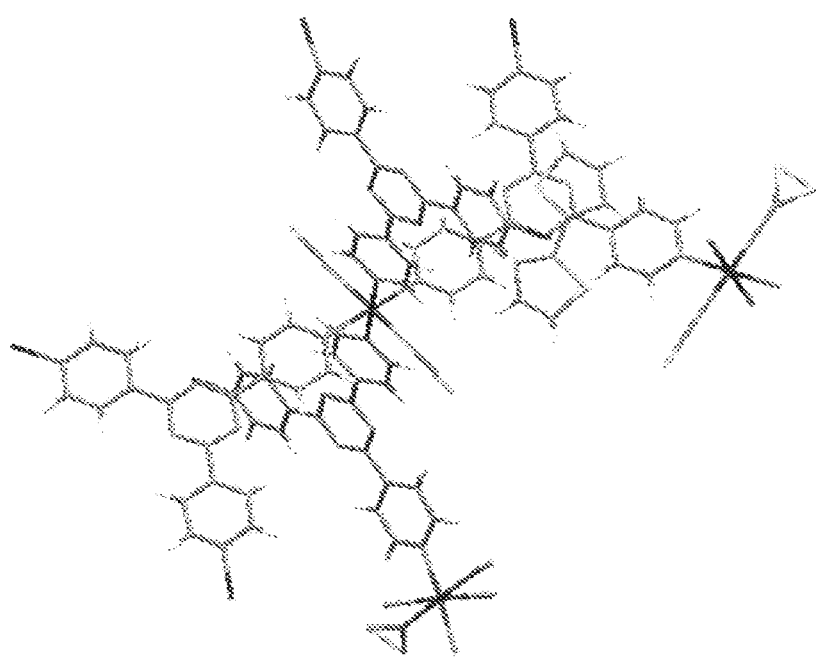
FIG. 23 is an enlarged view illustrating the polymer-metal complex including 2,2'-bithiophene obtained in Example 16.

Tables 8 shows the crystallographic data, and FIGS. 22 and 23 show the crystal structure. Note that the occupancy ratio of 2,2'-bithiophene was 100%.

TABLE 8

| Crystal system | Tetragonal |
| --- | --- |
| Space group | P42/mnm |
| a (Å) | 26.58 |
| b (Å) | 26.58 |
| c (Å) | 36.273 |
| α (°) | 90 |
| β (°) | 90 |
| γ (°) | 90 |
| Z | 16 |
| R1 | 11.08 |

Comparative Example 1

10 mg of the single crystal of the polymer-metal complex 1 obtained in the step 1 of Example 1 was immersed in 10 mL of cyclohexane for 2 days under the same conditions as those employed in the step 2 of Example 1 to obtain a single crystal 1r of a polymer-metal complex.

The resulting polymer complex was dissolved in hydrochloric acid, extracted with deuterated chloroform, and subjected to NMR measurement. As a result, only nitrobenzene and cyclohexane were observed in a ratio (cyclohexane:nitrobenzene) of 39:61.

A micro vial with a septum cap was charged with 50 μL of cyclohexane, and one piece (size: 150×130×120 μm, theoretical amount of a substance having a specific gravity of 1 required to fill the pores therewith: 1.17 μg) of the resulting single crystal was immersed in cyclohexane contained in the micro vial.

5,6,7,8-Tetramethoxy-2-(4-methoxyphenyl)-4H-1-benzopyran-4-one was dissolved in dichloromethane at a concentration of 1 μg/1 μL, and 5 μL of the resulting sample solution (including 5,6,7,8-tetramethoxy-2-(4-methoxyphenyl)-4H-1-benzopyran-4-one in an amount of 5 μg) was added to the micro vial. The value A in Comparative Example 1 was 3.3.

After fastening the cap on the micro vial, a pinhole was formed in the septum using a syringe needle (hole diameter: 0.8 mm), and the micro vial was allowed to stand in a temperature-controlled room at 45° C. for 2 days.

The organic solvent (cyclohexane and dichloromethane) contained in the micro vial volatilized at a volatilization rate of about 48 μL/24 hours under the above conditions, and the solution was concentrated.

The single crystal was then removed, mounted on an X-ray crystal structure analyzer, and subjected to crystal structure analysis.

Figure 24:
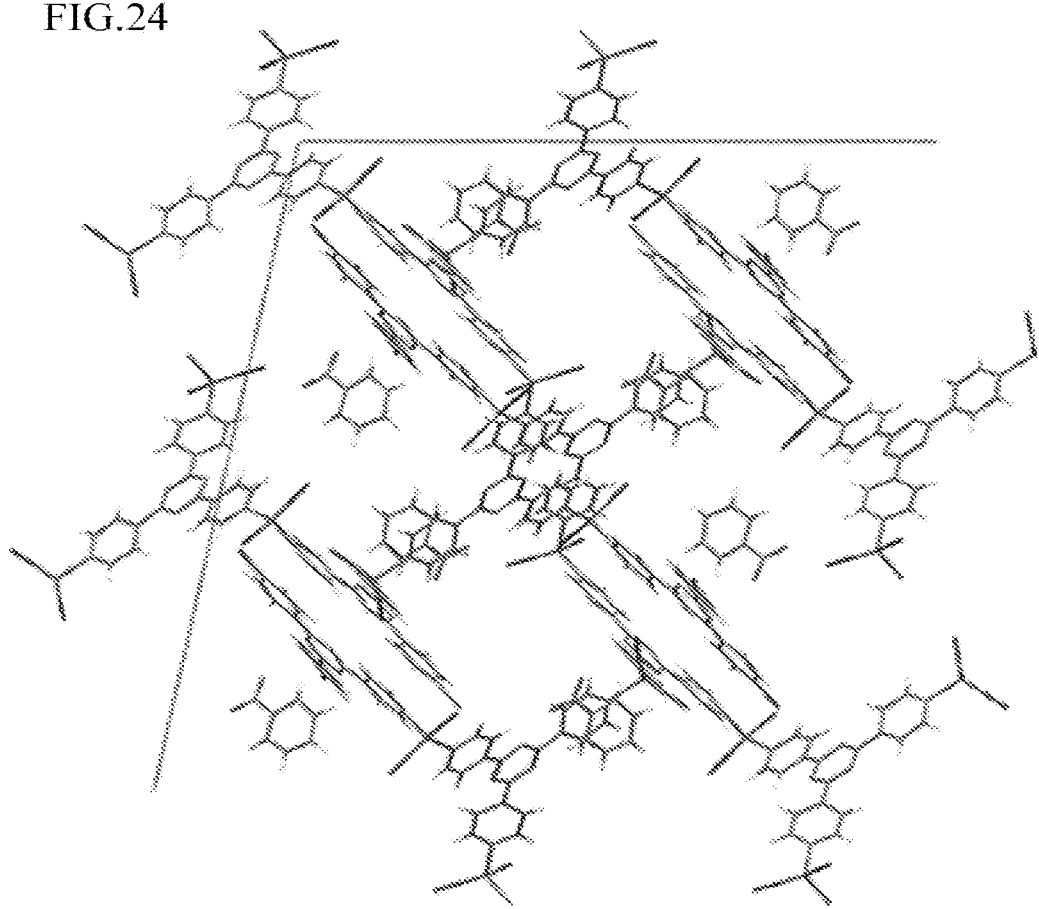
FIG. 24 is a view illustrating the polymer-metal complex obtained in Comparative Example 1.
Figure 25:
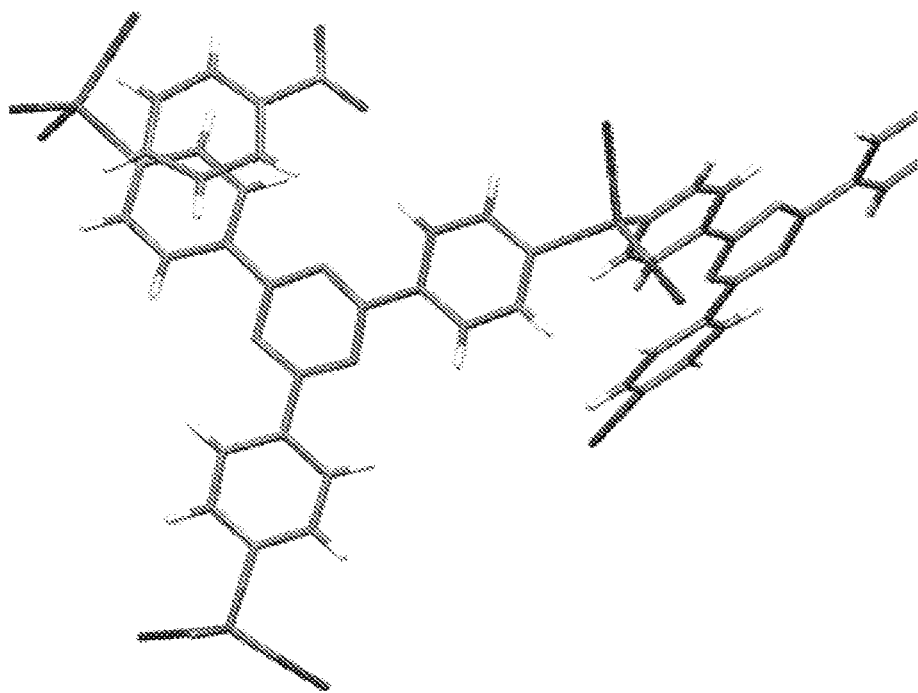
FIG. 25 is an enlarged view illustrating the polymer-metal complex obtained in Comparative Example 1.

Tables 9 shows the crystallographic data, and FIGS. 24 and 25 show the crystal structure.

It was found that nitrobenzene remained included in the crystal, and 5,6,7,8-tetramethoxy-2-(4-methoxyphenyl)-4H-1-benzopyran-4-one was not included in the crystal.

TABLE 9

| Crystal system | Monoclinic |
|---|---|
| Space group | C2/c |
| a (Å) | 34.534 |
| b (Å) | 15.033 |
| c (Å) | 30.376 |
| α (°) | 90 |
| β (°) | 101.559 |
| γ (°) | 90 |
| Z | 8 |
| R1 | 7.72 |

Comparative Example 2

An experiment was performed in the same manner as in Comparative Example 1, except that one piece (size: 150× 130×120 µm, theoretical amount of a substance having a specific gravity of 1 required to fill the pores therewith: 1.17 µg) of the single crystal of the polymer-metal complex 1 obtained in the step 1 of Example 1 was used.

A micro vial with a septum cap was charged with 50 µL of cyclohexane, and one piece of the single crystal was immersed in cyclohexane contained in the micro vial.

5,6,7,8-Tetramethoxy-2-(4-methoxyphenyl)-4H-1-benzopyran-4-one was dissolved in dichloromethane at a concentration of 1 µg/1 µL, and 5 µL of the resulting sample solution (including 5,6,7,8-tetramethoxy-2-(4-methoxyphenyl)-4H-1-benzopyran-4-one in an amount of 5 µg) was added to the micro vial. The value A in Comparative Example 2 was 3.3.

After fastening the cap on the micro vial, a pinhole was formed in the septum using a syringe needle (hole diameter: 0.8 mm), and the micro vial was allowed to stand in a temperature-controlled room at 45° C. for 2 days.

The organic solvent (cyclohexane and dichloromethane) contained in the micro vial volatilized at a volatilization rate of about 48 µL/24 hours under the above conditions, and the solution was concentrated.

The single crystal was then removed, mounted on an X-ray crystal structure analyzer, and subjected to crystal structure analysis.

A crystal structure in which nitrobenzene was included in the pores was obtained in the same manner as in Comparative Example 1.

Example 17

100 mg of the single crystal of the polymer-metal complex obtained in the step 1 of Example 1 was immersed in 10 mL of cyclohexane at 25° C. for 7 days to saturate the pores of the single crystal with cyclohexanone to obtain a polymer-metal complex crystal including cyclohexane.

As illustrated in FIG. 26, the polymer-metal complex crystal was placed on a glass plate, and one drop (about 100 µg) of isoprene (or cyclohexane) was dropped onto the complex using a dropper. The polymer-metal complex crystal was transferred to a micro vial with a septum cap (not illustrated in FIG. 26), and the micro vial was placed in a temperature-controlled room at 25° C. for 2 days to obtain a crystal structure analysis sample.

The resulting sample was removed, mounted on an X-ray crystal structure analyzer, and subjected to crystal structure analysis.

Figure 27:
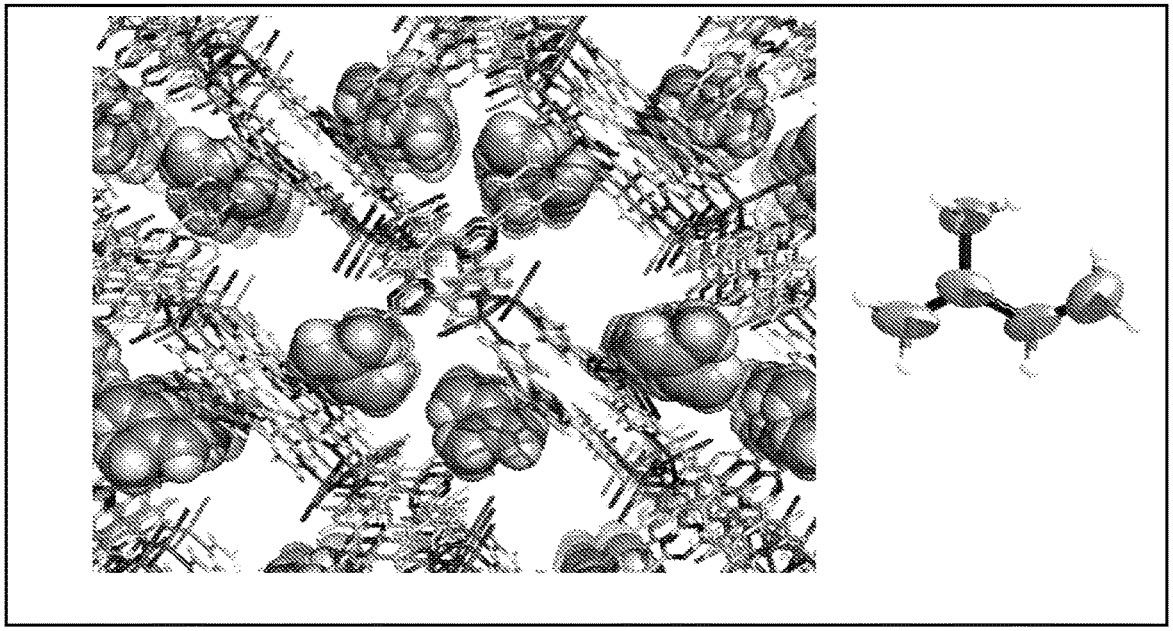
FIG. 27 is an enlarged view illustrating the crystal structure analysis sample (polymer-metal complex including isoprene) obtained in Example 17.

FIG. 27 is an enlarged view showing the crystal structure of the polymer-metal complex including isoprene.

Example 18

100 mg of the single crystal of the cobalt complex obtained in Example 9 was immersed in 10 mL of toluene at 25° C. for 7 days to saturate the pores of the single crystal with toluene to obtain a polymer-metal complex crystal including toluene.

As illustrated in FIG. 26, the polymer-metal complex crystal was placed on a glass plate, and one drop (about 100 µg) of cyclohexanone was dropped onto the complex using a dropper. The polymer-metal complex crystal was allowed to stand in a temperature-controlled room at 25° C. for 2 days to obtain a crystal structure analysis sample.

The resulting sample was removed, mounted on an X-ray crystal structure analyzer, and subjected to crystal structure analysis.

Figure 28:
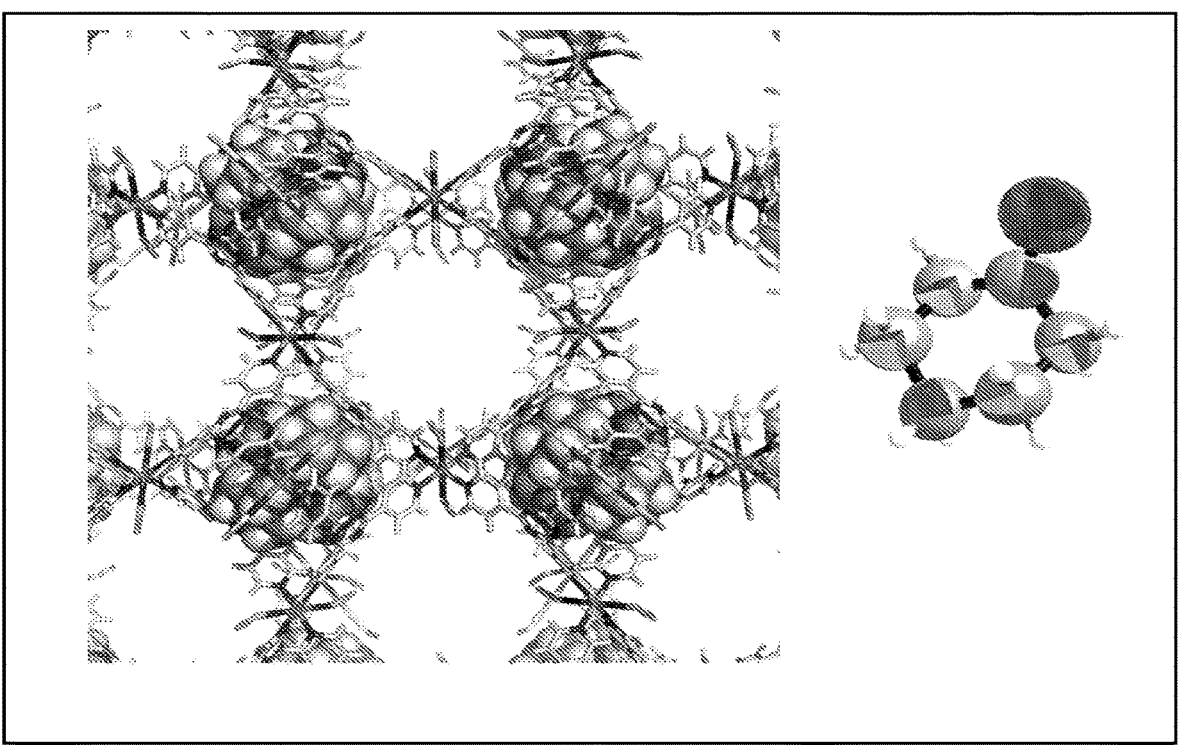
FIG. 28 is an enlarged view illustrating the crystal structure analysis sample (polymer-metal complex including cyclohexanone) obtained in Example 17.

FIG. 28 is an enlarged view showing the crystal structure of the polymer-metal complex including cyclohexanone.

It was confirmed from the results of Examples 17 and 18 that the crystal structure of a liquid organic compound could be analyzed in the same manner as that of a crystal.

REFERENCE SIGNS LIST

1: Crystal plane X
2: Crystal plane Y
3: Pore
4: Extension direction of pore
11: Cap (septum cap)
11a: Septum
11b: Plastic part
12: Opening (degassing hollow needle)
13: Container main body (vial)
14: Solvent solution of organic compound (α)
15: Single crystal of polymer-metal complex
16: Crystal support

The invention claimed is:
1. A method for preparing a crystal structure analysis sample in which a molecule of an organic compound for which a molecular structure is to be determined, is arranged in pores and voids of a polymer-metal complex crystal in an ordered manner, the method comprising:
    immersing a polymer-metal complex crystal including a guest compound in a solvent solution that includes the organic compound,
the polymer-metal complex crystal including a guest compound being the polymer-metal complex crystal comprising a polymer-metal complex that comprises a ligand having two or more coordinating moieties, and a metal ion that serves as a center metal, the polymer-metal complex having a three-dimensional network structure that is formed by the metal ion and the ligand that is coordinated to the metal ion, and having pores and voids that are three-dimensionally arranged in the three-dimensional network structure in an ordered manner, at least one compound selected from a group consisting of an aliphatic hydrocarbon, an alicyclic hydrocarbon, an ether, an ester, an aromatic hydrocarbon, a halogenated hydrocarbon, and a nitrile being included in the pores and the voids as a guest compound (A), and a ratio of an amount of the guest compound (A) present in the pores and the voids to a total amount of the guest compound included in the pores and the voids being 60 mol % or more.

2. The method for preparing a crystal structure analysis sample according to claim 1, the method comprising immersing the polymer-metal complex crystal including the guest compound (A) in the solvent solution that includes the organic compound in an amount of 100 μg or less so that a value A calculated by an expression (2) is 0.1 to 30, $$A = \frac{b}{a} \quad (2)$$

where, b is an amount of the organic compound included in the solvent solution, and a is an amount of a substance having a specific gravity of 1 that is required to fill all of the pores and the voids of the polymer-metal complex crystal with the substance having a specific gravity of 1.

3. The method for preparing a crystal structure analysis sample according to claim 1, wherein a concentration of the organic compound in the solvent solution is 0.001 to 50 μg/μL.

4. The method for preparing a crystal structure analysis sample according to claim 1, wherein the organic compound is impurities included in a compound derived from a natural product, or a synthetic compound.

5. The method for preparing a crystal structure analysis sample according to claim 1, the method comprising volatilizing the solvent after immersing the polymer-metal complex crystal including a guest compound in the solvent solution that includes the organic compound to concentrate the solvent solution.

6. The method for preparing a crystal structure analysis sample according to claim 5, wherein a volatilization rate of the solvent is 0.1 to 1000 μL/24 hours.

7. The method for preparing a crystal structure analysis sample according to claim 5, wherein the solvent is volatilized at 0 to 180° C.

8. The method for preparing a crystal structure analysis sample according to claim 1, wherein the immersing of the polymer-metal complex crystal including a guest compound in the solvent solution that includes the organic compound includes immersing one piece of the polymer-metal complex crystal including a guest compound in the solvent solution that includes the organic compound.

9. The method for preparing a crystal structure analysis sample according to claim 1, the method comprising:
a step (I) that separates a mixture that includes an organic compound for which a molecular structure is to be determined, by liquid chromatography to obtain a solvent solution of the organic compound for which the molecular structure is to be determined; and
a step (II) that immerses the polymer-metal complex crystal including a guest compound in the solvent solution of the organic compound for which the molecular structure is to be determined, that has been obtained in the step (I), and volatilizes the solvent under moderate conditions to concentrate the solvent solution.

10. The method for preparing a crystal structure analysis sample according to claim 1, wherein a molecular structure of the resulting crystal structure analysis sample can be determined with a resolution of at least 1.5 Å by applying MoKα radiation (wavelength: 0.71 Å) generated at a tube voltage of 24 kV and a tube current of 50 mA to the crystal structure analysis sample, and detecting diffracted X-rays using a CCD detector.

11. The method for preparing a crystal structure analysis sample according to claim 1, wherein the guest compound (A) is an alicyclic hydrocarbon having 3 to 20 carbon atoms or an aromatic hydrocarbon having 6 to 10 carbon atoms.

12. The method for preparing a crystal structure analysis sample according to claim 1, wherein the guest compound (A) is a saturated alicyclic hydrocarbon having 3 to 20 carbon atoms.

13. The method for preparing a crystal structure analysis sample according to claim 1, wherein a total occupancy ratio of the guest compound included in the pores and the voids of the polymer-metal complex is 10% or more.

14. The method for preparing a crystal structure analysis sample according to claim 1, wherein the ligand having two or more coordinating moieties is an organic ligand having three or more coordinating moieties, and the metal ion that serves as the center metal is a cobalt ion or a zinc ion.

15. The method for preparing a crystal structure analysis sample according to claim 1, wherein the polymer-metal complex is a compound represented by $[[M(X)_2]_3(L)_2]_n$ (wherein M is a metal ion, X is a monovalent anion, L is a tridentate ligand represented by a formula (1),

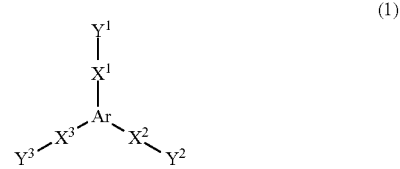

wherein Ar is a substituted or unsubstituted trivalent aromatic group, $X^1$ to $X^3$ are independently a divalent organic group, or a single bond that directly bonds Ar and $Y^1$, $Y^2$, or $Y^3$, and $Y^1$ to $Y^3$ are independently a monovalent organic group having a coordinating moiety, and n is an arbitrary natural number).

16. The method for preparing a crystal structure analysis sample according to claim 1, wherein the metal ion is an ion of a metal among the metals that belong to Groups 8 to 12 in the periodic table.

17. The method for preparing a crystal structure analysis sample according to claim 1, wherein the metal ion is a zinc(II) ion or a cobalt(II) ion.

18. The method for preparing a crystal structure analysis sample according to claim 1, wherein the polymer-metal complex crystal has a cubic or cuboidal shape with a side length of 10 to 1000 μm.

19. The method for preparing a crystal structure analysis sample according to claim 1, the method comprising immersing a polymer-metal complex crystal including a crystallization solvent in the guest compound (A) in a liquid state, or an inert solvent solution that includes the guest compound (A), the polymer-metal complex crystal including a crystallization solvent comprising a polymer-metal complex that comprises a ligand having two or more coordinating moieties, and a metal ion that serves as a center metal, the polymer-metal complex having a three-dimensional network structure that is formed by the metal ion and the ligand that is coordinated to the metal ion, and having pores and voids that are three-dimensionally arranged in the three-dimensional network structure in an ordered manner, a crystallization solvent (excluding the guest compound (A)) being included in the pores and the voids.

20. A method for determining a molecular structure of an organic compound comprising analyzing a crystal structure of a crystal structure analysis sample obtained using the method for preparing a crystal structure analysis sample according to claim 1 to determine a molecular structure of an organic compound included in the pores and the voids of the crystal structure analysis sample.

* * * * *